US008852640B2

(12) United States Patent
Hubbell et al.

(10) Patent No.: US 8,852,640 B2
(45) Date of Patent: Oct. 7, 2014

(54) MICELLES FOR DELIVERY OF NITRIC OXIDE

(75) Inventors: Jeffrey A. Hubbell, Morges (CH); Yun Suk Jo, Lausanne (CH); André van der Vlies, Zurich (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 974 days.

(21) Appl. No.: 12/217,507

(22) Filed: Jul. 3, 2008

(65) Prior Publication Data
US 2010/0003338 A1 Jan. 7, 2010

(51) Int. Cl.
A61K 9/14 (2006.01)
A61K 31/787 (2006.01)
A61K 9/107 (2006.01)
A61K 9/127 (2006.01)
A61K 47/48 (2006.01)
A61K 31/80 (2006.01)
A61K 31/77 (2006.01)

(52) U.S. Cl.
CPC .............. *A61K 31/77* (2013.01); *A61K 31/787* (2013.01); *A61K 9/1075* (2013.01); *A61K 9/1273* (2013.01); *A61K 47/48176* (2013.01); *A61K 47/488* (2013.01); *A61K 31/80* (2013.01); *Y10S 977/906* (2013.01)
USPC ..... 424/489; 424/78.23; 424/501; 514/772.5; 514/772.7; 977/906

(58) Field of Classification Search
None
See application file for complete search history.

(56) References Cited

U.S. PATENT DOCUMENTS

| | | | |
|---|---|---|---|
| 5,295,962 A | 3/1994 | Crocker et al. | |
| 5,421,826 A | 6/1995 | Crocker et al. | |
| 5,423,745 A | 6/1995 | Todd et al. | |
| 5,721,365 A * | 2/1998 | Keefer et al. | 544/382 |
| 5,833,658 A | 11/1998 | Levy et al. | |
| 6,147,068 A | 11/2000 | Smith et al. | |
| 6,720,350 B2 | 4/2004 | Kunz et al. | |
| 6,737,447 B1 | 5/2004 | Smith et al. | |
| 6,764,461 B2 | 7/2004 | Mickley et al. | |
| 7,303,574 B2 | 12/2007 | Sater | |
| 2003/0077243 A1 * | 4/2003 | Fitzhugh et al. | 424/78.27 |
| 2003/0147845 A1 | 8/2003 | Saavedra et al. | |
| 2005/0074506 A1 * | 4/2005 | Natan et al. | 424/718 |
| 2005/0079148 A1 | 4/2005 | Fitzhugh et al. | |
| 2007/0053952 A1 | 3/2007 | Chen et al. | |
| 2007/0196327 A1 | 8/2007 | Kalivretenos et al. | |
| 2007/0292471 A1 | 12/2007 | Hrabie et al. | |

FOREIGN PATENT DOCUMENTS

WO 9509612 A1 4/1995

OTHER PUBLICATIONS

JA Hrabie, JE Saavedra, PR Roller, GJ Southan, LK Keefer. "Conversion of Proteins to Diazeniumdiolate-Based Nitric Oxide Donors." Bioconjugate Chem, vol. 10, 1999, pp. 838-842.*
A Lavasanifar, J Samuel, GS Kwon. "Poly(ethylene oxide)-block-poly(L-amino acid) micelles for drug delivery." Advanced Drug Delivery Reviews, vol. 54, 2002, pp. 169-190.*
YS Jo, AJ van der Vlies, J Gantz, S Antonijevic, D Demurtas, D Velluto, JA Hubbell. "RAFT Homo- and Copolymerization of N-Acryloyl-Morpholine, Piperidine, and Azocane and Their Self-Assembled Structures." Macromolecules, vol. 41, 2008, pp. 1140-1150, Published Feb. 5, 2008.*
PG Parzuchowski, MC Frost, ME Meyerhoff. "Synthesis and Characterization of Polymetharcylate-Based Nitric Oxide Donors." Journal of the American Chemical Society, vol. 124, 2002, pp. 12182-12191.*
Babapulle et al., "Coated stents for the prevention of restenosis: Part I.", Circulation, 106:2734-2740 (2002).
Babapulle et al., "Coated scents for the prevention of restenosis: Part II", Circulation 106:2859-2866 (2002).
Herman, "Therapeutic potential of nitric oxide donors in the prevention and treatment of atherosclerosis", Eur. Heart J. 26, 1945-1955 (2005).
Jo et al., "Raft homo- and copolymerization of N-acryloyl-morpholine, piperidine, and azocane and their self assembled structures", Macromolecules, 41:1140-1150 (2008).
Vaughn et al., "Estimation of nitric oxide production and reaction rates in tissue by use of a mathematical model", Am J Physiol-Heart, C43:H2163-H2176 (1998).
Zhou et al., "Water-soluble poly(ethylenimine)-based nitric oxide donors: Preparation, characterization, and potential application in hemodialysis", Biomacromolecules, 7(9): 2565-2574 (2006).
Acharya et al., "Mechanisms of controlled drug release from drug-eluting stents", Adv. Drug Delivery Rev. 58, 387-401 (2006).
Davies et al., "Chemistry of the diazeniumdiolates. 2. Kinetics and mechanism of dissociation to nitric oxide in aqueous solution", J. Am. Chem. Soc., 123:5473-5481 (2001).
Drago et al., "Reaction of nitrogen(II) oxide with various primary and secondary amines", J. Am. Chem. Soc., 83: 1819-1822 (1961).
Duran et al., "Reduction of postoperative adhesions by N,O-carboxymethylchitosan and spermine NONOate in rats", Exp. Anim., 52:267-272 (2003).
Dzau et al, "Vascular proliferation and atherosclerosis: New perspectives and therapeutic strategies", Nat. Med. 8, 1249-1256 (2002).
Ettenson et al, "Local drug delivery: An emerging approach in the treatment of restenosis", Vasc. Med., 5: 97-102 (2000).
Herman et al., "Therapeutic potential of nitric oxide donors in the prevention and treatment of atherosclerosis", Eur. Heart J. 26, 1945-1955 (2005).
Horstmann, Ph.D., Dissertation, Friedrich-Schiller-Universität Jena, 2003.

(Continued)

*Primary Examiner* — Frederick Krass
*Assistant Examiner* — Isaac Shomer
(74) *Attorney, Agent, or Firm* — Dardi & Herbert, PLLC; Curtis B. Herbert

(57) ABSTRACT

Embodiments include a vehicle for delivery of nitric oxide comprising: a collection of micelles having an internal micelle core that comprises a polymer with N-diazeniumdiolate comprising NO complexed with secondary amines of the polymer. Embodiments include a method of making a nitric oxide vehicle comprising dissolving a polymer that comprises secondary amines in an aqueous solution and combining the polymer with nitric oxide in the solution to form a N-diazeniumdiolate comprising the nitric oxide complexed with the secondary amines, with the formation of the N-diazeniumdiolate causing the polymer to be at least partially insoluble in the solution and to form a collection of micelles that have an internal core that comprises N-diazeniumdiolate.

21 Claims, 26 Drawing Sheets

(56) References Cited

OTHER PUBLICATIONS

Jo et al., "RAFT homo- and copolymerization of N-acryloyl-morpholine, piperidine, and azocane and their self-assembled structures", Macromolecules, 41:1140-1150 (2008).

Keefer et al., "Chemistry of the Diazeniumdiolates I. Structural and spectral characteristics of the [N(O)NO]- functional group", Nitric Oxide-Biol. Chem., 5:377-394 (2001).

Lamas et al., "Nitric oxide: From discovery to the clinic", Trends Pharmacol. Sci., 19:436-438 (1998).

Lancaster, "A tutorial on the diffusibility and reactivity of free nitric oxide", Nitric Oxide-Biol. Chem., 1:18-30 (1997).

Lee et al., "An evaluation of the roles of metabolic denitrosation and α-hydroxylation in the hepatotoxicity of N-nitrosodimethylamine", Chem. Res. Toxicol., 9:1319-1324 (1996).

Bohl Masters et al., "Effects of nitric oxide releasing poly(vinyl alcohol) hydrogel dressings on dermal wound healing in diabetic mice", Wound Repair Regen., 10:286-294 (2002).

Moncada et al. "The discovery of nitric oxide and its role in vascular biology", Br. J. Pharmacol. 147:S193-S201 (2006).

Parzuchowski et al., "Synthesis and characterization of polymethacrylate-based nitric oxide donors", J. Am. Chem. Soc., 124: 12182-12191 (2002).

Popowich et al., "Nitric oxide: What a vascular surgeon needs to know", Vascular 15:324-335 (2007).

Pulfer et al., "Incorporation of nitric oxide-releasing crosslinked polyethyleneimine microspheres into vascular grafts", J. Biomed. Mater. Res., 37:182-189 (1997).

Ross, "Atherosclerosis—an inflammatory disease", N. Engl. J. Med., 340:115-126 (1999).

Rothrock et al., "Synthesis of nitric oxide-releasing gold nanoparticles", J. Am. Chem. Soc., 127:9362-9363 (2005).

Schainfeld, "Potential emerging therapeutic strategies to prevent restenosis in the peripheral vasculature", Catheter. Cardiovasc. Interv., 56: 421-431 (2002).

Snyder, "Classification of the solvent properties of common liquids", J. Chromatogr., A92:223-230 (1974).

Srinivasan et al., "Chemistry of the diazeniumdiolates. 3. Photoreactivity", J. Am. Chem. Soc., 123:5465-5472 (2001).

Vaughn et al., "Estimation of nitric oxide production and reaction rates in tissue by use of a mathematical model", Am J Physiol-Heart, 274:H2163-H2176 (1998).

Weintraub, "The pathophysiology and burden of restenosis", Am. J. Cardiol., 100: 3K-9K (2007).

Westedt et al., "Deposition of nanoparticles in the arterial vessel by porous balloon catheters: Localization by confocal laser scanning microscopy and transmission electron microscopy", AAPS Pharmsci., 4:1-6 (2002).

Westedt et al., "Poly(vinyl alcohol)-graft-poly(lactide-co-glycolide) nanoparticles for local delivery of paclitaxel for restenosis treatment. ", J. Control. Release, 119:41-51 (2007).

Zhang et al., "Nitric oxide-releasing fumed silica particles: Synthesis, characterization, and biomedical application", J. Am. Chem. Soc., 125:5015-5024 (2003).

Zheng et al., "Design, synthesis, and evaluation of novel bifunctional iron-chelators as potential agents for neuroprotection in alzheimer's, parkinson's, and other neurodegenerative diseases", Bioorg. Med. Chem. 13:773-783 (2005).

Zhou et al., "Water-soluble poly(ethylenimine)-based nitric oxide donors: Preparation, characterization, and potential application in hemodialysis", Biomacromolecules 7:2565-2574 (2006).

* cited by examiner

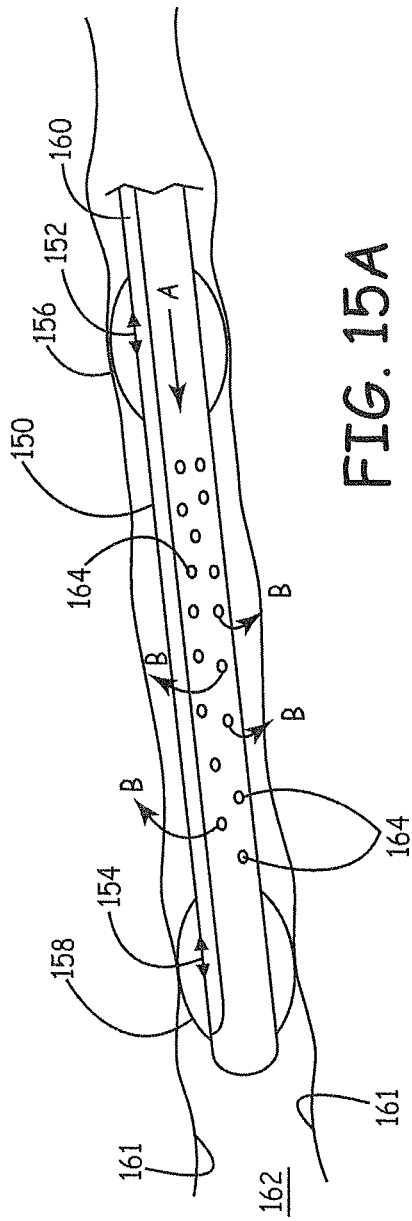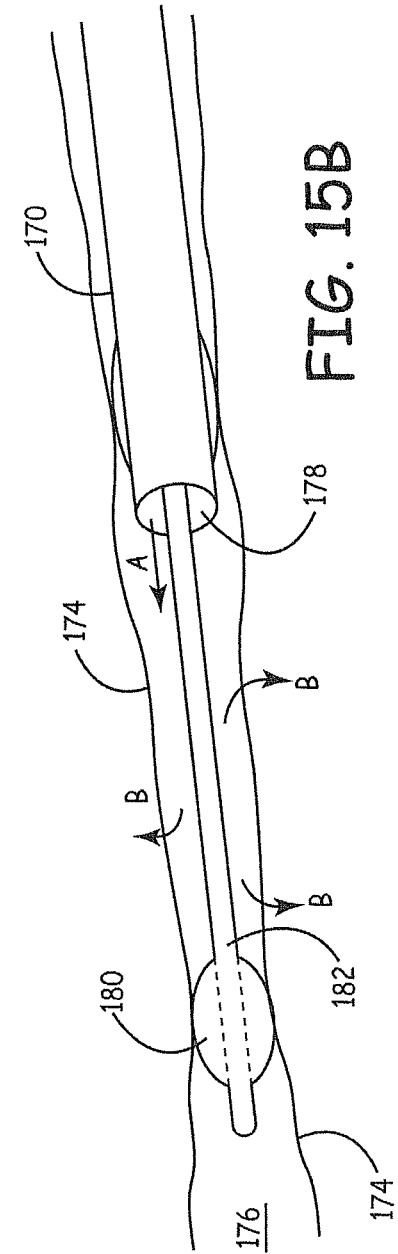

MICELLES FOR DELIVERY OF NITRIC OXIDE

BACKGROUND

Drug delivery is an important consideration for achieving therapeutic uses of a drug. The drug must be delivered to a patient in a useful form and arrive at its intended destination in a patient in a form that can interact with its target.

SUMMARY AND INTRODUCTION TO THE INVENTION

Block copolymeric amphiphiles are useful for absorption of a number of drug classes within the cores formed by self-assembly of a typically hydrophobic block in water. Described herein is an alternative concept, where complexation of a drug with a water-soluble block of a diblock copolymer drives micellization. Specifically, nitric oxide (NO), a potent regulator in wide variety of blood and tissue responses[1,2] was complexed to secondary amines in an AB diblock copolymer, driving the formation of micelles. The AB diblock copolymer was designed and researched to be soluble in water but insoluble after complexing with NO. Further insights were required to make the resulting complex of NO and polymer make micelles, with the internal core of the micelles having the NO and shielding the NO from water, or alternatively introducing moieties that would allow for water to penetrate quickly enough to accelerate release but slowly enough to extend a half-life of the rate of release of the NO. Liberation of the NO makes the copolymer become water soluble again so that it may be readily cleared by the patient's body. The very small micellar self-assemblies formed after conversion of secondary amines into N-diazeniumdiolates, termed NONOation, are capable of penetrating complex tissue structures, such as the arterial media, thus creating new medical applications by allowing for delivery of NO to various tissue targets for the first time.

While other NO donor systems release their complexed NO very quickly[3-6], water, and thus proton, exclusion from the micelle cores described herein delayed release to a half-life of about 7 days. Copolymerization to yield a more hydrophilic micelle core accelerated release.

NO is therapeutically useful. In the context of cardiovascular medicine, coronary arterial atherosclerosis is closely related to endothelial dysfunction and pathophysiologically altered homeostasis[7,8]. Surgically, percutaneous transluminal coronary angioplasty (PTCA) is performed to restore blood flow in occluded lesions but is hampered by post-PTCA restenosis due to the mechanical stimuli of dilation and interactions with the stent[9,10]. To prevent post-PTCA restenosis, conventional approaches have focused on local drug delivery with inhibitors of cell migration and proliferation[11,12]. Endogenous NO generated from endothelial nitric oxide synthase (eNOS) physiologically induces endothelial-dependent relaxation of blood vessels and modulates the tone of arterial vascular smooth muscle cells (VSMCs)[13,14]. NO is difficult to deliver directly, so it is conventionally delivered as a prodrug, referred to as a NO donor; yet most NO donors decompose too fast to be useful as an anti-restenotic drug, which may require NO release over a few weeks after deployment of a stent[12,15,16]. Furthermore, the lifetime of NO in tissues is a mere 4-15 seconds, corresponding to a diffusion distance of about 150 to about 500 microns (μm), rendering stent-based delivery to the thick arterial media impossible[17,18].

In contrast, described herein are NO-releasing micelles, which release NO at a sufficiently slow rate, are sufficiently small to penetrate tissues under mild pressure (e.g. less than about 100 nm), and are self-assembled structures that can be eventually dissembled and secreted after all NO has been delivered. One mechanism of action may be that the hydrophobic microenvironment in the micelle core protects a reservoir of NO complex from protons diffusing from the surroundings and thus delay proton-catalyzed NO liberation. To form a self-assembled core-shell structure, a pro-amphiphilic diblock copolymer was designed. Reversible addition-fragmentation transfer (RAFT) polymerization, a living radical polymerization, was employed to synthesize well-defined block copolymers. As reported earlier[19], various analogues of acrylamides with cyclic secondary amine side chains have been successfully homo- and co-polymerized using RAFT polymerization with excellent control and narrow polydispersity. Herein, certain embodiments are a hydrophobic poly(N-diazeniumdiolate) (polyNONOate) formed by complexation of NO to a poly(secondary amine) block, the poly(secondary amine) being water soluble but yielding an insoluble poly (NONOate).

One embodiment of the invention is a vehicle for NO delivery. This vehicle includes a collection of micelles having an internal micelle core that comprises a polymer with N-diazeniumdiolate comprising NO complexed with secondary amines of the polymer.

The micelles may be internally free of water, meaning that there is essentially no detectable water in the micelle core. Alternatively, the micelles may be prepared in embodiments that are merely depleted of water. Water has a concentration of about 55 molar. The fact that the micellar core can be prepared to be essentially free of water is deduced from the fact that the micelles can be prepared with an NO half life of, e.g., about a week, more than about four orders of magnitude more than the few seconds otherwise observed. Micelles made with hydrophilic moieties having a lesser half-life than a week but still much more than a few seconds points to the internal water as being depleted as opposed to essentially absent. Depleted of water is thus a term that refers to more than 0% water but much less than 55 molar of water, and is quantifiable at least by observing NO half-lives. Accordingly, some embodiments are micellar collections prepared to be internally free of water, e.g., to achieve a specified NO release rate, or are internally depleted of water to achieve an alternatively specified NO release rate.

In some embodiments, micelles are prepared with a polymer that comprises piperazine moieties that contribute the secondary amines that form the N-diazeniumdiolate. An example of a piperazine moiety is:

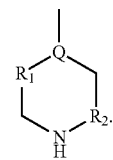

Piperazine moiety wherein Q- is a linker to the polymer, and R1 or R2 are groups independently selected to be $CH_2$, $CH_3CH_2$, or $CH_3CH$. The linker depends upon the polymer the moiety is attached to. For instance, Q may comprise C, N, or S groups. The bond of Q- may be single, double, or triple, as suited to the overall linker chemistry. Linkers can be, for example, comprised of one or more of: ether group, ester group, amide group, acrylamide group, thioester group, sulfide group, amidosulfide group, urea group, carbonate group, acrylate group, carbamate group, oxime group, epoxide group, imine group, enamine group, and the like. In general, a secondary amine on a ring may be used. Exemplary rings include rings having 3 to 12 moieties that form the ring. The ring may have one of more amines. A ring compound can covalently bear other substituent groups such as alkane, alkene group, alkyne group, alcohol group, acrylamide group, acrylate group, vinyl group, aldehyde group, ketone group, carboxylate group, carbonate group, carbamate group, sulfide group, sulfoamide group, sulfonate group, sulphate group, phosphate group, borate group, imine group (iminium), oxime group, and the like. The rings may be homologous or heterocyclic, meaning a cyclic compound having as a ring member at least two different elements. Substitution is liberally allowed on the chemical groups, and on the atoms that occupy a position in a formula depicted herein, for various physical effects on the properties of the compounds, such as mobility, sensitivity, solubility, compatibility, stability, and the like, as is known generally in the art. The term group indicates that the generically recited chemical entity (e.g., alkyl group, alkenyl group, aromatic group, epoxy group, arylamine group, aromatic heterocyclic group, aryl group, alicyclic group, aliphatic group, heterocyclic non-aromatic group etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromopropyl, and the like. However, as is consistent with such nomenclature, no substitution would be included within the term that would alter the fundamental bond structure of the underlying group.

The polymer may be a block copolymer comprising a plurality of polymeric blocks (meaning at least two, e.g., three or more). At least one of the blocks may be a hydrophilic polymer and a second block being a polymer that comprises the secondary amines. Examples of hydrophilic polymers are poly(N-acryloylmorpholine), polyethylene glycol (PEG), polyvinylpyrrolidone, polyvinyl alcohol, polyethyleneimine, polyacrylic acid, or copolymers of the same (including block copolymers or copolymers of the mers used to make of the listed homopolymers). PEG is a term referring to a polymer with —CH$_2$CH$_2$O— repeats, regardless of the actual end-groups of the polymer. Some of the blocks may further be copolymeric.

In general, it is useful for the polymer to be water-soluble when free of complexed nitric oxide and water-insoluble when complexed with the nitric oxide. The change from solubility to solubility can, for instance, be used to drive micellization. Water soluble is a term meaning at least about 1 gram of material dissolves in one liter of water; slightly water soluble means that more than about 0.1 gram per liter of the material is soluble in a liter of water but less than about 1 gram of material can be dissolved in a liter of water; water-insoluble means that less than 0.1 gram of the material is soluble in a liter of water. The solubility of a polymer in water is a significant physical property of the polymer. In general, polymers described herein as hydrophobic are polymers that are relatively more hydrophobic than other polymers in the micelles. Hydrophilic polymers are more hydrophilic relative to other polymers in the micelle and are water soluble in isolation, i.e., before crosslinking or otherwise being bonded to other polymers.

A half-life of release of NO from the micelles can be predetermined and varied as described herein. Examples of half lives are from about 1 day to about 30 days, or from about ten minutes to about 30 days; artisans will immediately appreciate that all the ranges and values within the explicitly stated ranges are contemplated, e.g., from about 1 hour to about 48 hours, less than about 7 days, more than about ten minutes, more than about 1 hour, or from about 48 hours to about 12 days.

The collections of micelles can be prepared with a mean diameter from, e.g., about 10 nm to about 200 nm; artisans will immediately appreciate that all the ranges and values within the explicitly stated ranges are contemplated, e.g., from about 20 nm to about 70 nm, about 55 nm, or from about 25 nm to about 100 nm. Larger particles of more than about 200 nm mean diameter may also be prepared, with these particles being termed microparticles herein since they begin to approach the micron scale and fall approximately within the limit of optical resolution. The size distribution of such a collection of particles can be controlled so that a coefficient of variation (standard deviation divided by mean particle size) around a mean diameter of a collection of the particles may be less than about 50, about 35, about 20, about 10, or about 5 nm; artisans will immediately appreciate that all the ranges and values within the explicitly stated ranges are contemplated.

The micelles may be dried micelles and/or frozen micelles. The term micelle refers to the particles formed in an aqueous solution generally having a core and shell structure, with the core being a congregation of water-insoluble or slightly water-soluble moieties and the shell being relatively more water-soluble than the core. The term micelle as used herein, does not require the solution phase to be present; i.e., the micelles can be isolated from the solution that they are made in. One method of isolation is to freeze the solution with the micelles and remove the water, e.g., by lyophilization, leaving the particles. The term dried micelles thus refers to micelles that may or may not have water in them, but are not in solution or suspension. Dried micelles may subsequently be resuspended, put in a new solution, or mixed with other materials, e.g., as in a coating, gel, paste, salve, or other medium. Some embodiments, however, include the micelles suspended in a pharmaceutically acceptable aqueous carrier, with pharmaceutically acceptable excipients being well known.

In use, micelles may be provided to a patient by a method comprising introducing to the patient, e.g., by injection, orally, buccaly, as a suppository, transdermally, transdermal patch, or topically, e.g., by ointment or salve. Introducing the micelles to the patient in some embodiments comprises delivering the micelles across a tissue surface of a patient under pressure.

Other embodiments relate to using the micelles in a coating. The micelles can be mixed, suspended, dissolved, and/or dispersed in the coating. Hydrophilic coatings made with polymers that are at least slightly water soluble can allow for diffusion of the micelles through the coating. Or degradation of the coating may alternatively release, or enhance release, or the micelles.

Methods of making the micelles are described in detail. In general, some embodiments relate to dissolving a polymer that comprises secondary amines in an aqueous solution and combining the polymer with nitric oxide in the solution to form a N-diazeniumdiolate comprising the nitric oxide complexed with the secondary amines, with the formation of the N-diazeniumdiolate causing the polymer to be at least partially insoluble in the solution and to form a collection of micelles that have an internal core that comprises N-diazeniumdiolate.

BRIEF DESCRIPTION OF THE FIGURES

FIG. 15A is a cross-section of a first embodiment of a catheter for delivering micelles or other materials to a tissue; and FIG. 15B is a cut-away view of a lumen of a vessel depicting a second embodiment of a catheter for delivering micelles or other materials to a tissue.

DETAILED DESCRIPTION OF PREFERRED EMBODIMENTS

Figures 1A, 1B:
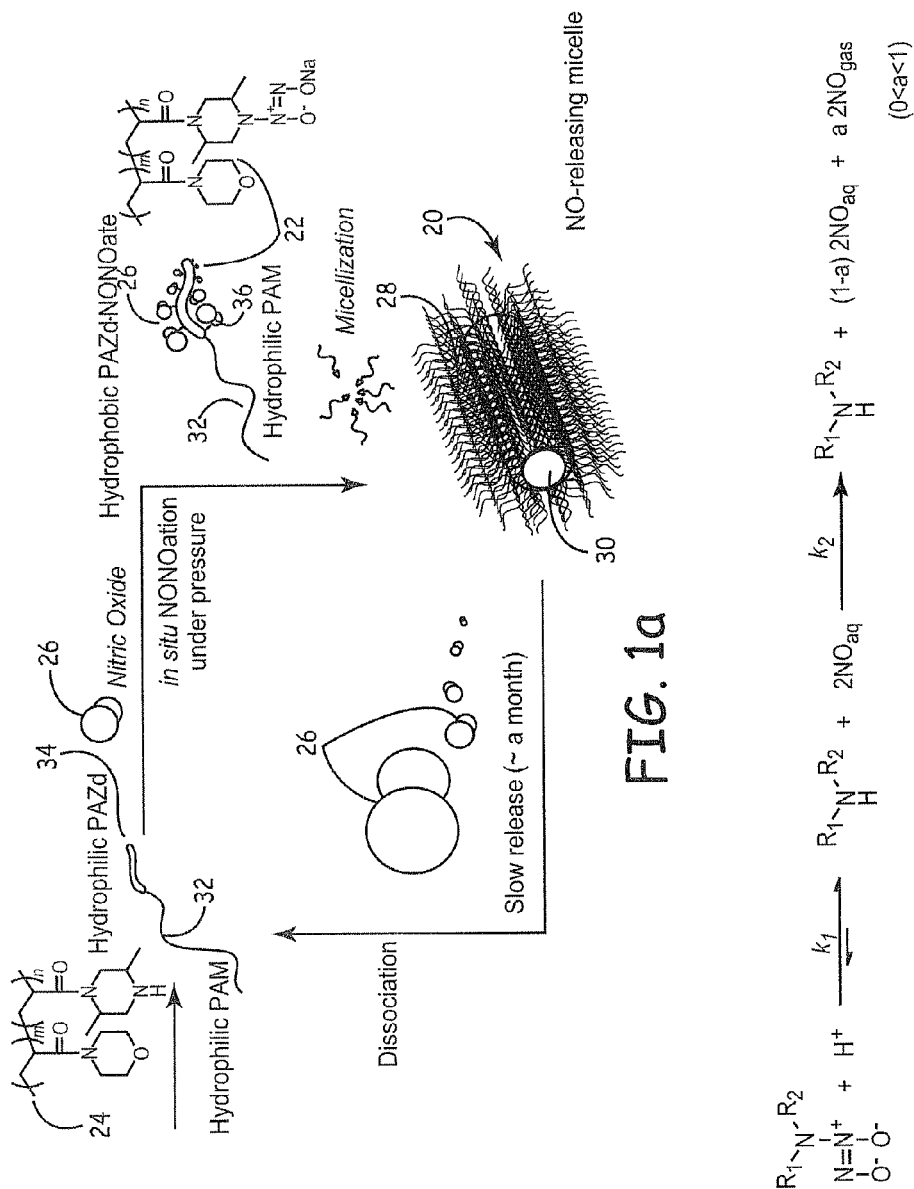
FIG. 1a depicts an embodiment for in situ formation of micelles and nitric oxide (NO) release from NONOate, with subscripts to PAM-PAZd•NONOate that denote the degree of polymerization.
FIG. 1b depicts kinetic equations of nitric oxide (NO) release from NONOate dissociation of diazen-1-ium-1,2-diolate (NONOate) and releasing NO.

Homopolymeric polyNONOates were synthesized to determine (in)solubility, and then an amphiphilic diblock copolymer containing polyNONOate was synthesized with poly(N-acryloylmorpholine) (PAM) as a hydrophilic block. The PAM block served to obtain micellization rather than precipitation as the hydrophilic poly(secondary amine) was complexed with NO to form the hydrophobic poly(NON-Oate). Three polyNONOates were prepared from monomers in the family of piperazine (a 6-member ring) with different number of carbons and/or substituents on the cyclic ring (see Schemes 1-2). The polyNONOate was then derived from the poly(secondary amine) after protection and deprotection during and after synthesis by reaction with NO; tert-Butoxycarbonyl (Boc) chemistry was used to protect the secondary amine-containing monomer during RAFT polymerization, which was later deprotected to restore the secondary amine groups in the polymer. From solubility tests, both poly(sodium 1-(N-acryloylpiperazin-1-yl)diazen-1-ium-1,2-diolate) (PAZ.NONOate) and poly(sodium 1-(N-acryloylhomopiperazin-1-yl)diazen-1-ium-1,2-diolate) (PAZh.NONOate) (see Table 1 for structures) were soluble in water, yet insoluble in any other organic solvent (see Table 2a-b). Therefore, neither of PAZ.NONOate nor PAZh.NONOate was considered as a suitable candidate for the hydrophobe of self-assembled aggregates after NONOation. In contrast, poly(sodium 1-(N-acryloyl-2,5-dimethylpiperazin-1-yl)diazen-1-ium-1,2-diolate) (PAZd.NONOate) was insoluble in water in distinction from its water-soluble precursor, poly(N-acryloyl-2,5-dimethylpiperazine) (PAZd) (see Table 2c). Thus, PAZd, selected as the pro-hydrophobic block NO acceptor, was copolymerized with PAM (see Scheme 3). The soluble poly[(N-acryloylmorpholine)-block-(N-acryloyl-2,5-dimethylpiperazine)] (PAM-PAZd) diblock copolymer was reacted with NO in deoxygenated water under a pressurized NO supply (see Scheme 5). As more amine groups of PAZd are gradually NONOated, the PAZd.NONOate block segregates more from the PAM block. In this way, in situ formation of aggregates of poly[(N-acryloylmorpholine)-block-(sodium 1-(N-acryloyl-2,5-dimethylpiperazin-1-yl)diazen-1-ium-1,2-diolate)] (PAM-PAZd.NONOate) is affected in aqueous media (FIG. 1a). As a result, PAM-PAZd.NONOate was self-assembled into micelles, as shown in transmission electron microscopy (TEM) images with 2% negative staining using uranyl acetate (FIG. 2a-c).

Referring to FIG. 1, depicted is a scheme of in situ formation of micelles and kinetic equations of nitric oxide (NO) release from NONOate. FIG. 1a depicts in situ formation of micelles 20 using, e.g., poly[(N-acryloylmorpholine)-block-(sodium 1-[4-acryloyl-2,5-dimethylpiperazin-1-yl]diazen-1-ium-1,2-diolate)] (22, PAM-PAZd•NONOate) under pressurized nitric oxide (NO) supply. PAM-PAZd, 24, the precursor of PAM-PAZd•NONOate is synthesized by RAFT polymerization followed by end group modification, deprotection, and basification steps. The polymer is soluble in water. In situ aggregate formation is carried out under 150 psi of NO for 5 d, which forms a hydrophobic NONOate on the PAZd block. $PAM_{142}$-PAZd•NONOate$_{23}$ micelles 22 reversely release NO 26 with around 1 wk of half-life under physiological conditions as determined by radical analyzer. Micelle 20 has shell 28 and core 30. Hydrophilic PAM blocks are indicated at 32, hydrophilic PAZ is indicated at 34, and PAZ•NONOate is indicated at 36. FIG. 1b depicts dissociation of diazen-1-ium-1,2-diolate (NONOate) and releasing NO. NO analyzer detects the level of $NO_{aq}$. Subscripts to PAM-PAZd•NONOate denote the degree of polymerization.

Figure 2:
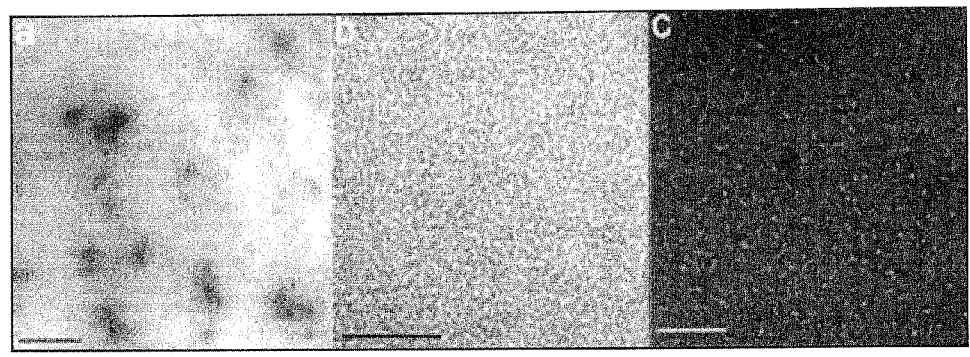
FIG. 2a is a photomicrograph of micelles of PAM146-PAZd•NONOate57; scale bar represents 500 nm.
FIG. 2b is a photomicrograph of micelles of PAM146-PAZd•NONOate23 micelles; scale bar represents 500 nm.
FIG. 2c is a photomicrograph of micelles of PAM142-PAZd•NONOate23; scale bar represents 500 nm.

Referring to FIG. 2, poly[(N-acryloylmorpholine)-block-(sodium 1-[4-acryloyl-2,5-dimethylpiperazin-1-yl]diazen-1-ium-1,2-diolate)] (PAM-PAZd•NONOate) micelles were formed in situ with hydrodynamic diameter of between 50 and 100 nm in average: (a) $PAM_{146}$-PAZd•NONOate$_{57}$ micelles, (b) $PAM_{146}$-PAZd•NONOate$_{23}$ micelles, and (c) $PAM_{142}$-PAZdNONOate$_{23}$ micelles. (From part a to part c, scale bar represents 500 nm). Over time in the electron beam, NONOate degradation and evolution of bubbles can be observed (not shown). Subscripts to PAM-PAZd•NONOate denote the degree of polymerization.

The morphology of the formed micelles generally depends on the block length ratio between the two polymer blocks, higher hydrophobic block ratios giving bigger hydrodynamic diameters than lower ones. Longer hydrophilic blocks yielded longer worm-like micelles: $PAM_{146}$-PAZd•NONOate$_{57}$ yielded longer worm-like micelles (ca. 110 nm) than did $PAM_{146}$-PAZd•NONOate$_{23}$ (ca. 80 nm) (FIG. 2 and Table 1). Despite the copolymer comprising a smaller fraction of hydrophobe, PAZd•NONOate$_{23}$, than hydrophile, $PAM_{146}$, spherical micelles were not the dominant in morphology, but rather worm-like micelles. However, with excess amount of base, ca. 10-20 times, micelles, namely $PAM_{142}$-PAZd•NONOate$_{23}$ tended to form spherical micelles and/or shorter worm-like micelles (FIG. 2c), with around 50 nm average diameter, as confirmed by dynamic light scattering (DLS) and TEM. Without being bound to a particular theory, it seems that during NONOation, some fraction of the base, here sodium methoxide, is partly neutralized by nitric/nitrous acid generated from NO reacting with trace oxygen and that NONOation may not be completed. Thus, the worm-like morphology dominant in $PAM_{146}$-PAZd•NONOate$_{23}$ could be a continuum toward spherical micelles, $PAM_{142}$-PAZd•NONOate$_{23}$. The size of $PAM_{142}$-PAZd•NONOate$_{23}$ is almost same as micelles prepared from the precursor, poly[(N-acryloylmorpholine)-block-(1-Boc-4-acryloyl-2,5-dimethylpiperazine)] ($PAM_{142}$-BocPAZ$_{23}$) (i.e., without deprotection of the secondary amine) (average diameter: 47±1.1 nm).

According to the chemical equation in FIG. 1b, the release kinetics of NO can be formulated in Eqs 1-3.

$$[A] = A_0 e^{-k_1 t} \quad (1)$$

$$[B] = \frac{2A_0 k_1}{k_2 - k_1}[e^{-k_1 t} - e^{-k_2 t}] \quad (2)$$

$$[C] = \frac{2A_0}{k_2 - k_1}[k_1(e^{-k_2 t} - 1) - k_2(e^{-k_1 t} - 1)] \quad (3)$$

where, [A] is the concentration of poly(NONOate), [B] is the concentration of $NO_{aq}$, [C] is the concentration of $NO_{gas}$, $k_1$ and $k_2$ are the kinetic constants. $A_0$ is the initial concentration of poly(NONOate).

Figure 3A:
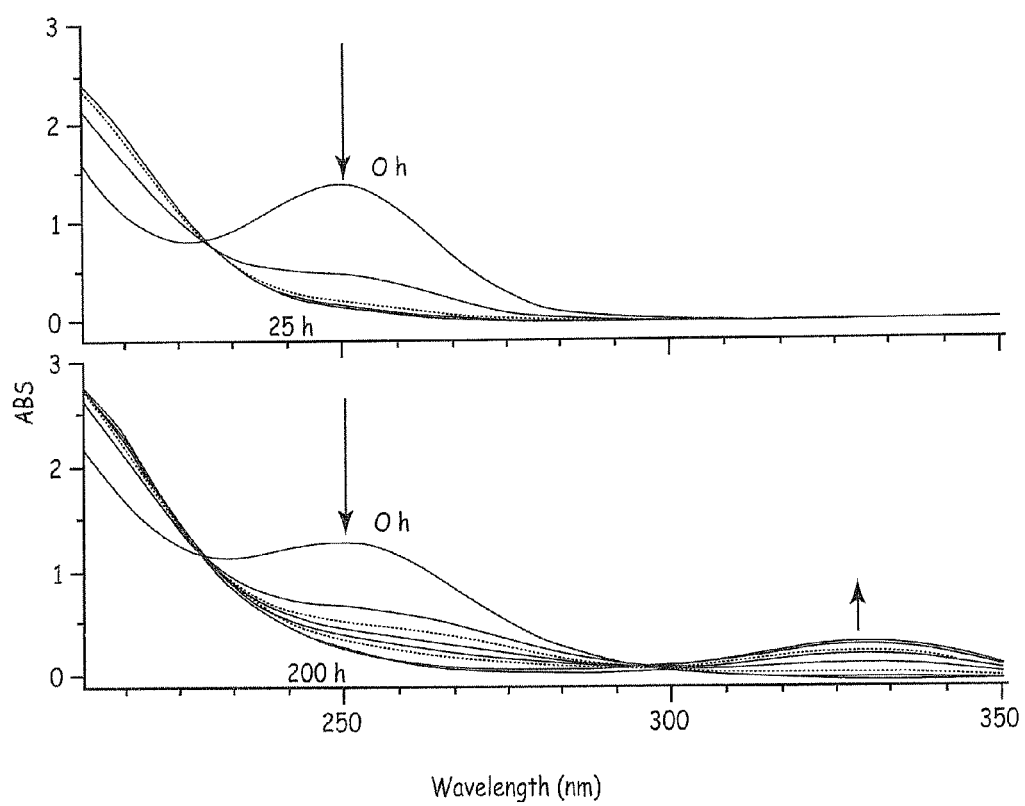
FIG. 3a is a UV absorbance profile over time for PAZ•NONOate (top) and PAZh•NONOate (bottom), showing that homopolymers release nitric oxide (NO) faster than micelles, the arrows indicate the evolution of the profile over time. ($\lambda$max=250 nm for PAZ•NONOate, $\lambda$max=250, 330 nm for PAZh•NONOate)
Figure 3B:
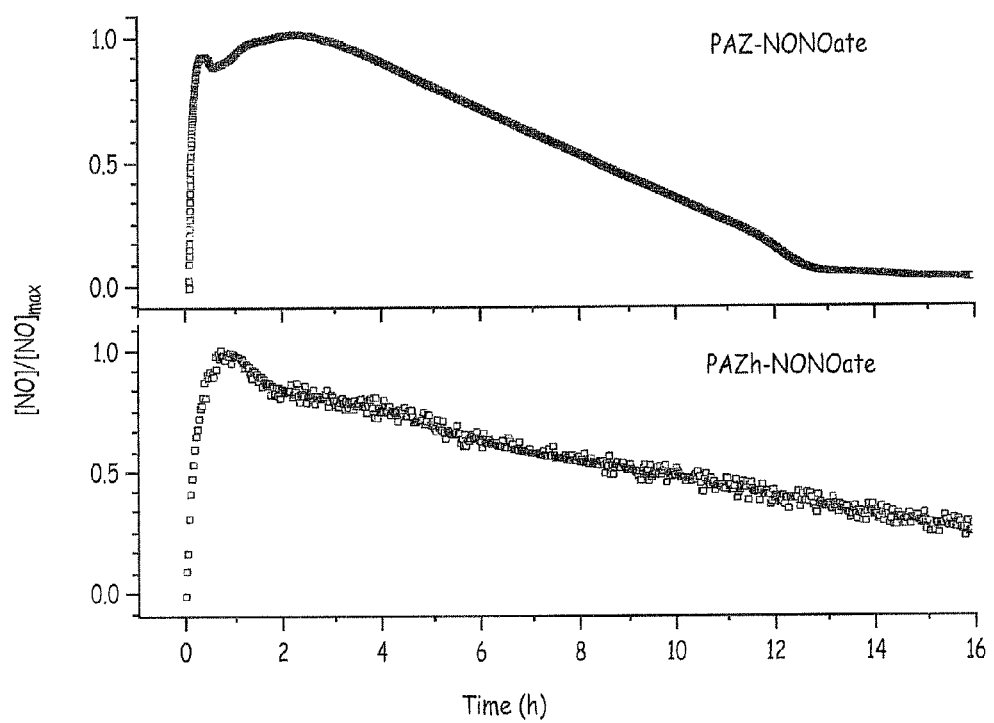
FIG. 3b is a plot of NO release from PAZ•NONOate (top) and PAZh•NONOate (bottom) as monitored by an NO analyzer over time at 37° C. in PBS (10 nm, pH 7.4)
Figure 3C:
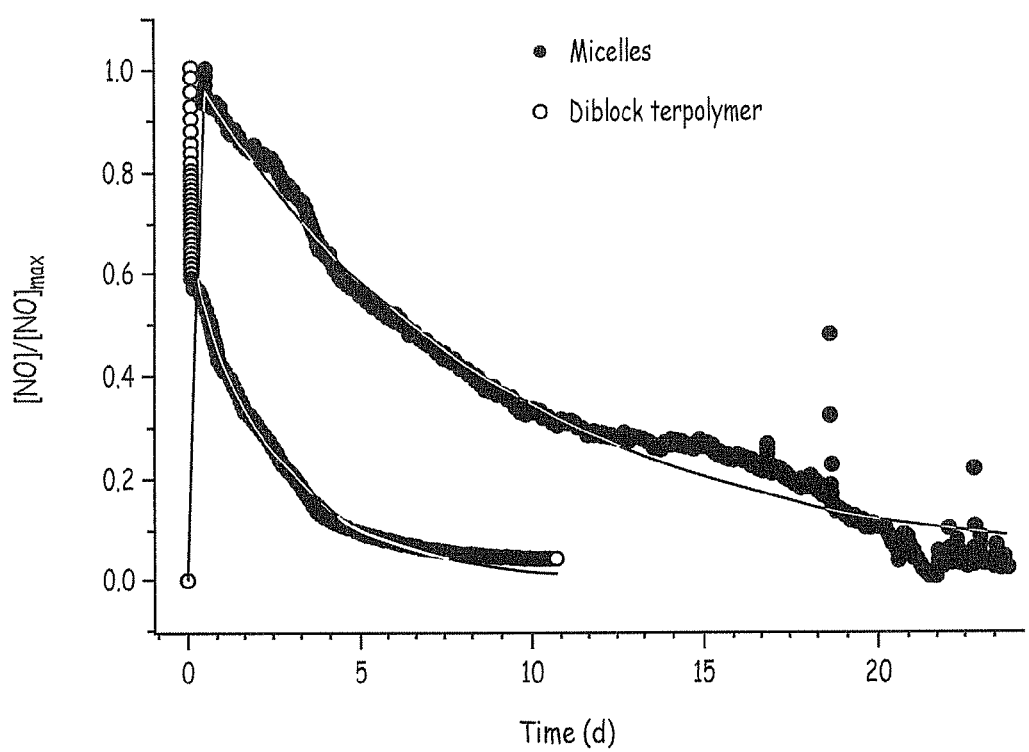
FIG. 3c is a plot of NO release from PAM142-PAZd•NONOate23 micelles monitored by NO analyzer over time at 37° C. in PBS (10 nm, pH 7.4) and PAM142-b1-(PAM2.5-r-PAZd•NONOate23) terpolymer.
Figure 3D:
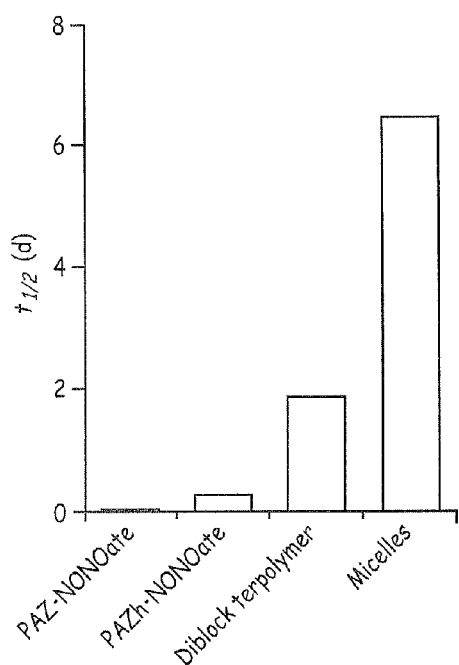
FIG. 3d is a bar graph of half-lives of homopolymers (PAZ•NONOate and PAZh•NONOate, both of which are soluble), PAM142-PAZd•NONOate23 micelles, and PAM142-b1-(PAM2.5-r-PAZd•NONOate23) terpolymer.
Figure 3E:
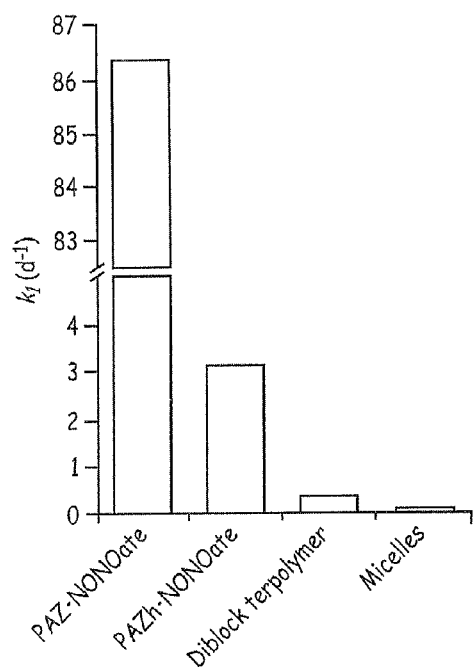
FIG. 3e is a bar graph of kinetic constants (k1) of dissociation of NONOate groups of homopolymers (PAZ•NONOate and PAZh•NONOate), PAM142-PAZd•NONOate23 micelles, PAM142-b1-(PAM2.5-r-PAZd•NONOate23) terpolymer.
Figure 13A:
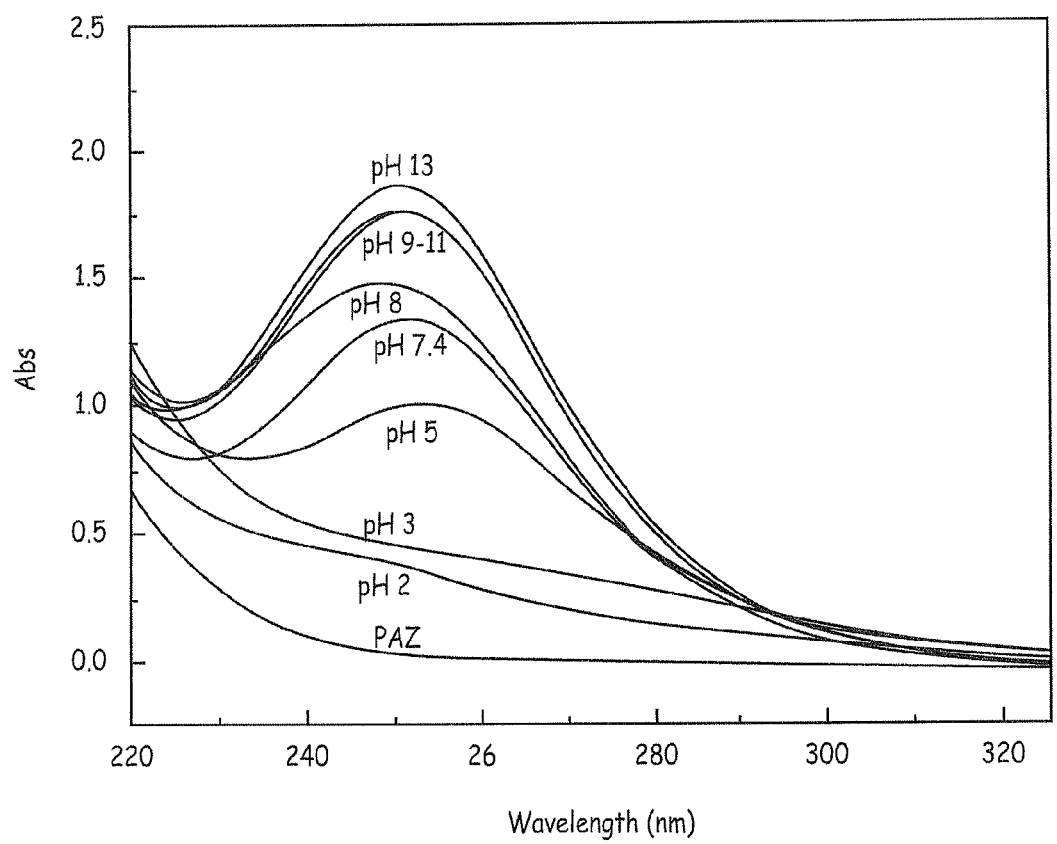
FIG. 13 shows pH and temperature dependence of NO release from PAZ•NONOate: a) UV absorbance spectra of PAZ•NONOate at time zero in different buffer ranging from pH 2 to pH 13. b) UV absorbance at 250 nm is plotted as a function of pH. c) UV absorbance spectra of PAZ•NONOate at time zero in different temperatures. d) UV absorbance at 250 nm is plotted as a function of temperature.
Figure 13B:
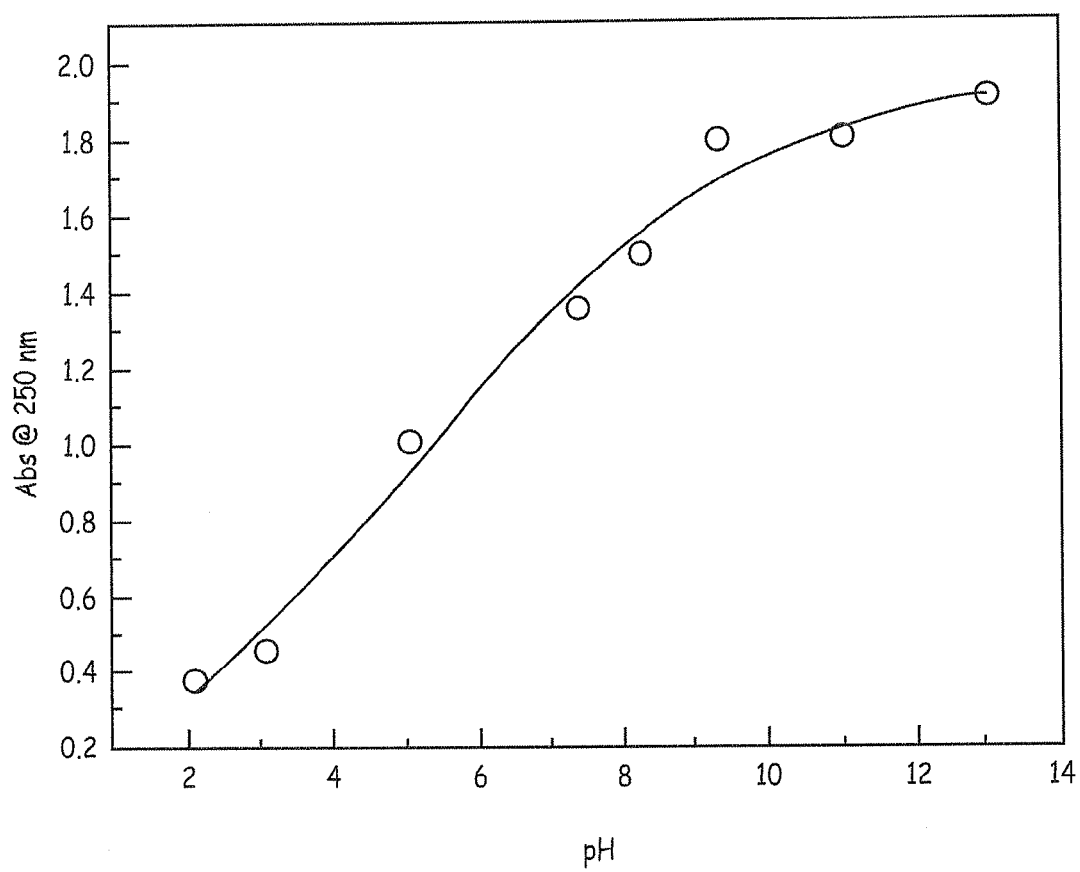
Figure 13C:
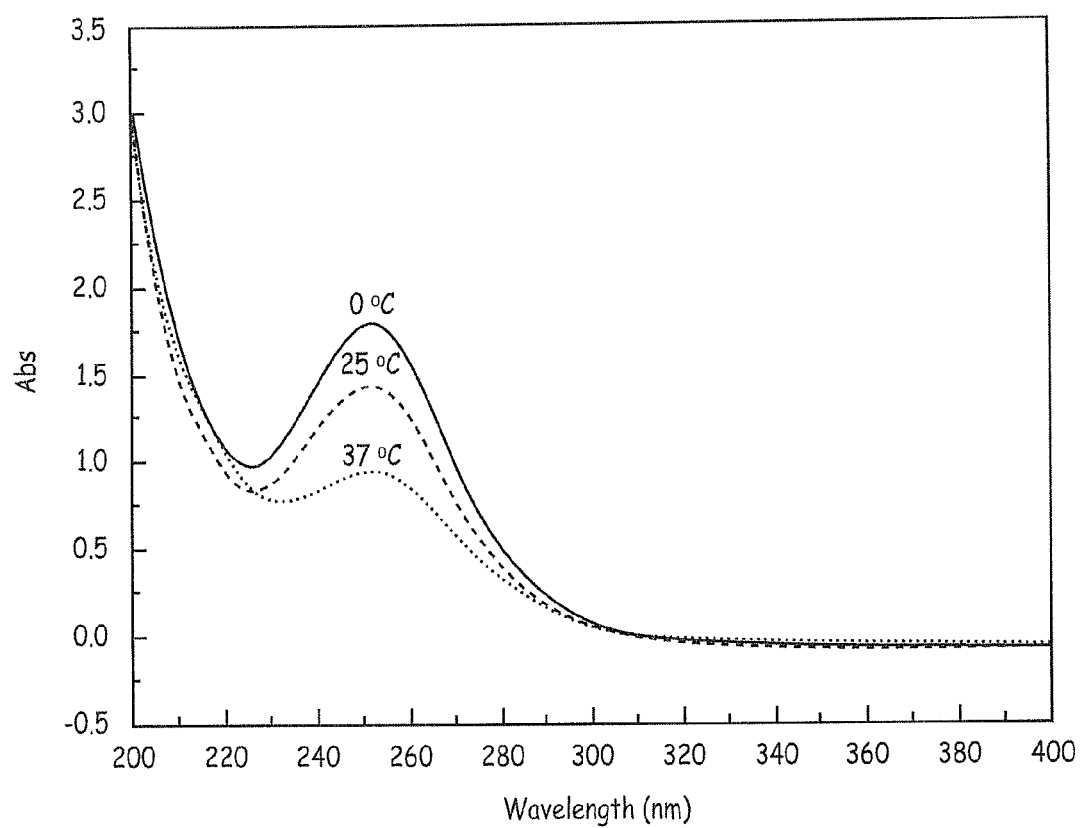
Figure 13D:
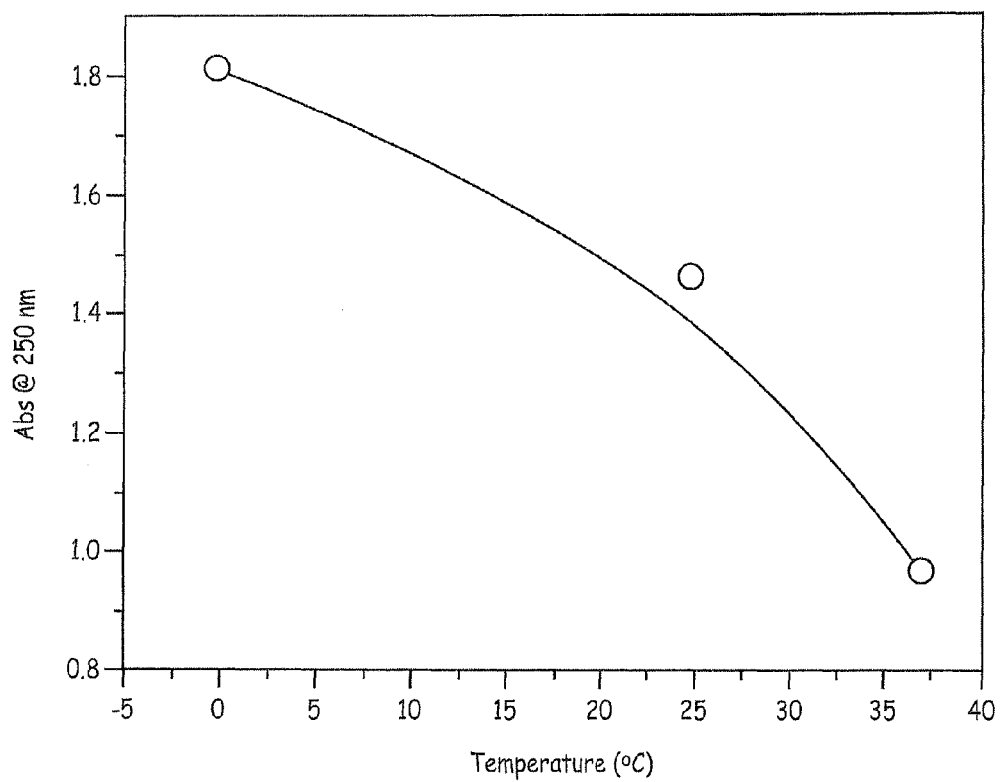

UV spectra of water-soluble PAZ•NONOate and PAZh•NONOate show distinct maxima at a wavelength 250 nm, which is typical for N-diazeniumdiolate (NONOate) groups[20-22]. As shown in FIG. 3a, the maxima at 250 nm decreases over time, which is common for water-soluble polyNONOates, suggesting NONOate groups are decomposed over time in phosphate-buffered saline (PBS; 10 mM, pH 7.4). At elevated pH, the maximum observance at 250 nm appears higher than lower pH due to spontaneous release of NO in contact with water (see FIG. 13a-b). At lower temperature, e.g. 0° C., the maxima at 250 nm decreased more slowly than at 37° C. (see FIG. 13c-d).

Referring to FIG. 3, results showed that homopolymers released NO faster than micelles. FIG. 3a shows UV absorbance profile over time for PAZ•NONOate (top) and PAZh•NONOate (bottom). Arrows indicate the evolution of the profile over time. ($\lambda_{max}$=250 nm for PAZ•NONOate, $\lambda_{max}$=250, 330 nm for PAZh•NONOate) FIG. 3b shows NO release from PAZ•NONOate (top) and PAZh•NONOate (bottom) monitored by an NO analyzer over time at 37° C. in PBS (10 nm, pH 7.4). FIG. 3c shows NO release from $PAM_{142}$-PAZd•NONOate$_{23}$ micelles monitored by NO analyzer over time at 37° C. in PBS (10 nm, pH 7.4) and $PAM_{142}$-bl-($PAM_{2.5}$-r-PAZd•NONOate$_{23}$) terpolymer. FIG. 3d shows half-lives of homopolymers (PAZ•NONOate and PAZh•NONOate, both of which are soluble), $PAM_{142}$-PAZd•NONOate$_{23}$ micelles, and $PAM_{142}$-bl-($PAM_{2.5}$-r-PAZd•NONOate$_{23}$) terpolymer. FIG. 3e shows kinetic constants ($k_1$) of dissociation of NONOate groups of homopolymers (PAZ•NONOate and PAZh•NONOate), $PAM_{142}$-PAZd•NONOate$_{23}$ micelles, $PAM_{142}$-bl-($PAM_{2.5}$-r-PAZd•NONOate$_{23}$) terpolymer PAZh•NONOate is decomposed more slowly than PAZ•NONOate, as observed from the change of the UV spectrum. Moreover, analogous to PAZh•NONOate, another new peak at 330 nm evolves over time, which is attributed to N-nitroso-compound formation[23,24]. To more precisely evaluate the release kinetics of NO under physiological conditions, the NO generated from lyophilized polymers was monitored in PBS (10 mM, pH 7.4) using an NO analyzer over the entire release period (FIG. 3b). According to Eqs 1 and 2, the half-life of $NO_{aq}$ generated from polyNONOate ($t_{1/2}$) can be calculated from the kinetic constant ($k_1$). As summarized in Table 1, PAZ•NONOate shows a half-life of 17 min, substantially longer than reported for a monomeric piperazine-based NONOate ($t_{1/2}$=5 mins)[25]. The release rate of NO from monomeric NONOate is substantially influenced by the substituents on the ring[25]. The longer release pattern observed with the soluble poly(NONOate)s is probably due to a more structurally hindered conformation of the NONOate groups grafted in the polymer chains.

Notably, there is also a remarkable difference in the half-life of NO release between PAZ•NONOate and PAZh•NONOate. At 37° C., NO release from PAZh•NONOate is far slower than from PAZ•NONOate (Table 1), suggesting that the addition of one more carbon in the 7-membered ring greatly affects the release rate of NO. This can also be explained by the structural difference influencing the hydrophobicity of the surrounding NONOate groups, slowing the proton transfer rate to NONOates due to the presence of the additional carbon in the 7-membered rings.

NO can be released from PAM-PAZd•NONOate micelles. Worm-like micelles, namely $PAM_{142}$-PAZd•NONOate$_{23}$, release NO strikingly slower than PAZ•NONOate or PAZh•NONOate; releasing NO over 3 weeks (FIG. 3 and Table 1). This effect can be attributed to the core-shell structure according to the intended design. For instance, the release pattern of PAZd•NONOate homopolymer was revealed to be extremely stable under physiological conditions. This result suggests the poor water solubility of PAZd•NONOate does not allow water molecules and thus protons to penetrate through the bulky (precipitate) particles of PAZd•NONOate.

To confirm that the mechanism of prolonged NO liberation from the micelles, a terpolymer was synthesized with PAM as one block and a randomly copolymerized (less) hydrophobic block, composed of PAM and PAZd•NONOate: poly[(N-acryloylmorpholine)-block-((N-acryloylmorpholine)-ran-(sodium 1-(N-acryloyl-2,5-dimethylpiperazin-1-yl)diazen-1-ium-1,2-diolate))] ($PAM_{142}$-bl-($PAM_{2.5}$-r-PAZd•NONOate$_{23}$)). Because the hydrophobic core of diblock terpolymer contains more hydrophilic constituent, PAM, the terpolymer became unstable to be assembled as micelles so as to be in unimolecular state and thus the diffusion rate of water molecules and protons to the NONOate moieties in the core or in the unimers will be higher than in the diblock copolymer with the (more) hydrophobic core. Terpolymer showed remarkably slower release rate than two water-soluble polyNONOates, ca. 1.9 day half-lives (FIG. 3 and Table 1), yet distinctively faster than PAM-PAZd•NONOate micelles. These results indicate that the core-shell micellar structure protects NO-bound hydrophobic moieties in the core and thus such a strikingly slow release pattern can be achieved from PAM-PAZd•NONOate micelles.

Figure 4A:
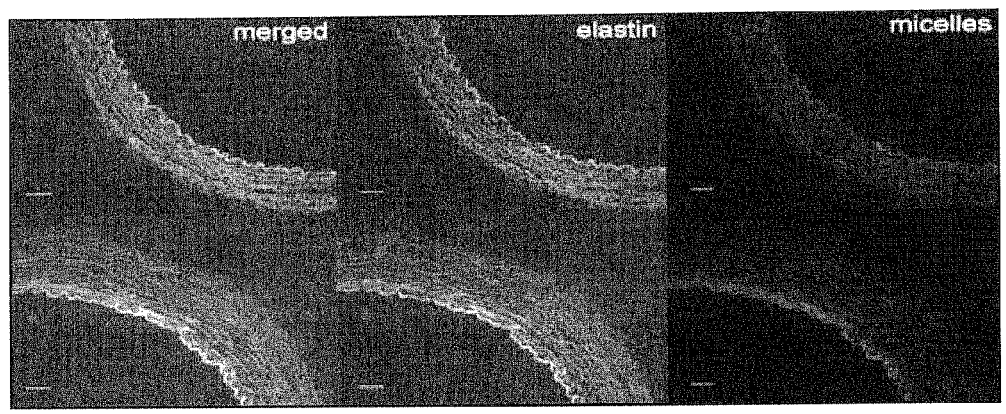
FIG. 4A is a photomicrograph with panels a-f showing poly[(N-acryloylmorpholine)-b1(sodium 1-[4-acryloyl-2,5-dimethylpiperazin-1-yl]diazen-1-ium-1,2-diolate)] (PAM-PAZd•NONOate) are infused ex vivo and shown to penetrate the arterial intima and media. Fluorescence microscopy images are taken from rabbit carotid artery after ex vivo infusion of coumarin-labeled PAM146-PAZd•NONOate23 micelles. Images from part (a) to part (c) represent for the artery infused under static conditions (1 atm for 1 min). Images from part (d) to part (f) represent the pulsed condition (1 atm for 10 s repeated 10 times). Images of part (b) and part (d) are from auto-fluorescent elastin in the artery. Images of part (c) and part (e) are from coumarin-labeled PAM146-PAZd•NONOate23 micelles. Images of part (a) and part (c) are merged with the signals from auto-fluorescent elastin and coumarin-labeled micelles infused.
Figure 4B:
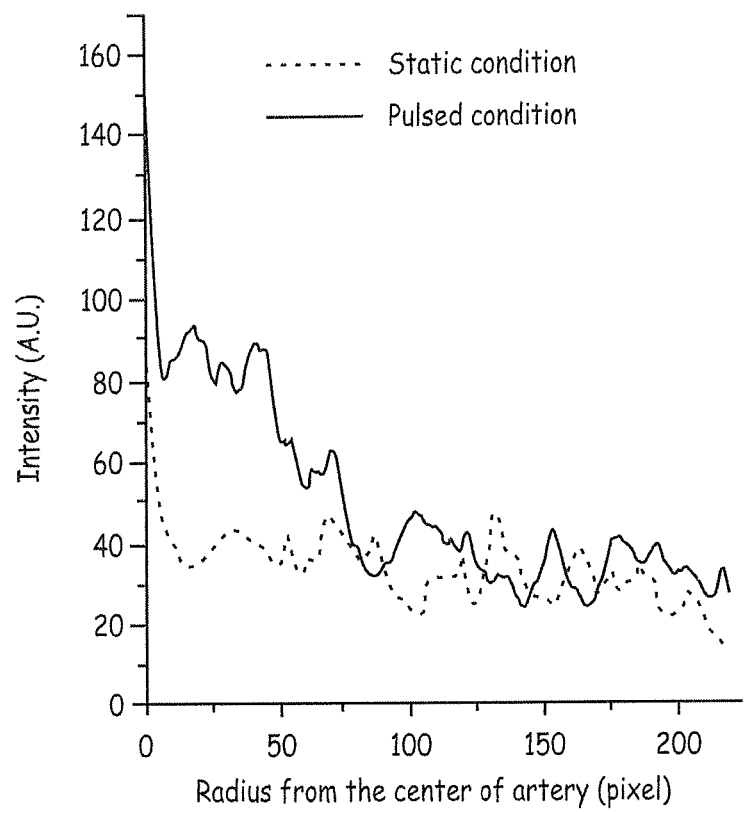
FIG. 4B is a graph of the embodiment of FIG. 4A that represents the distribution of the coumarin-labeled micelles across the rabbit carotid artery, with the intensity values being an average of 4 different places from the images and the intensity of fluorescence calculated by an image processor.
Figure 5A:
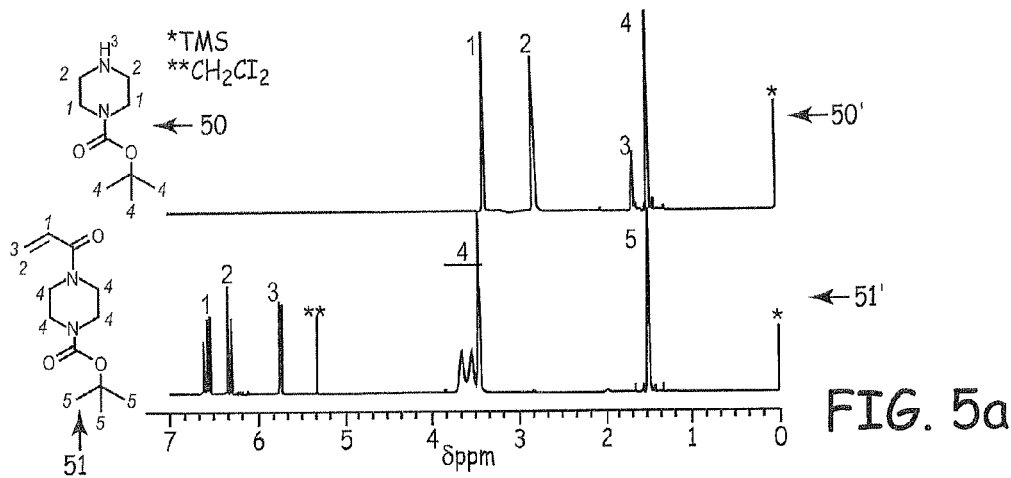
FIG. 5a shows 1H NMR (400 MHz, CDCl3) spectra (50', 51') of BocZ (50, top) and BocAZ (51, bottom), respectively.
Figure 5B:
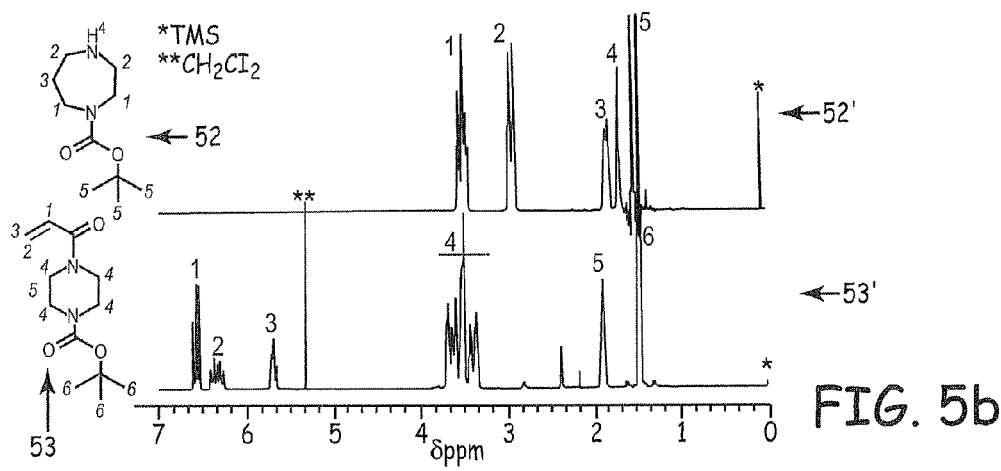
FIG. 5b shows 1H NMR (400 MHz, CDCl3) spectra (52', 53') of BocZh (52, top) and BocAZh (53, bottom), respectively.
Figure 5C:
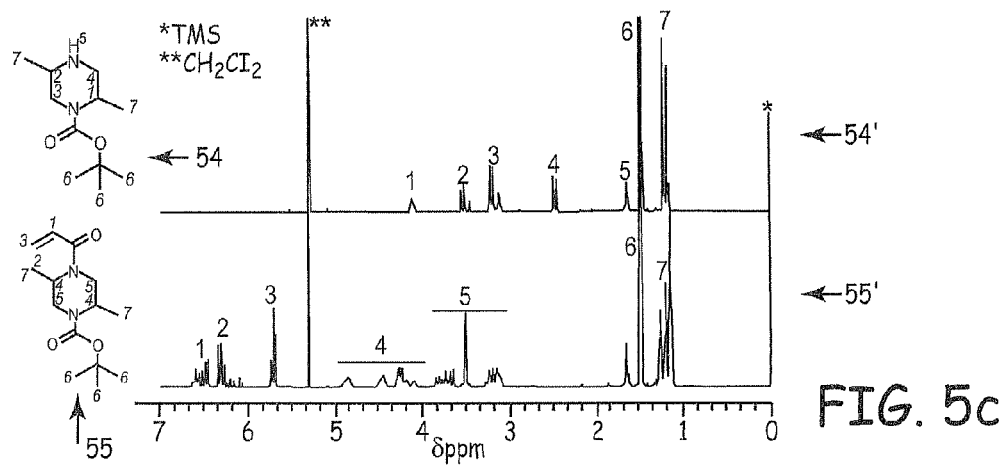
FIG. 5c shows 1H NMR (400 MHz, CDCl3) spectra (54', 55') of BocZd (54, top) and BocAZd (55, bottom)
Figure 6A:
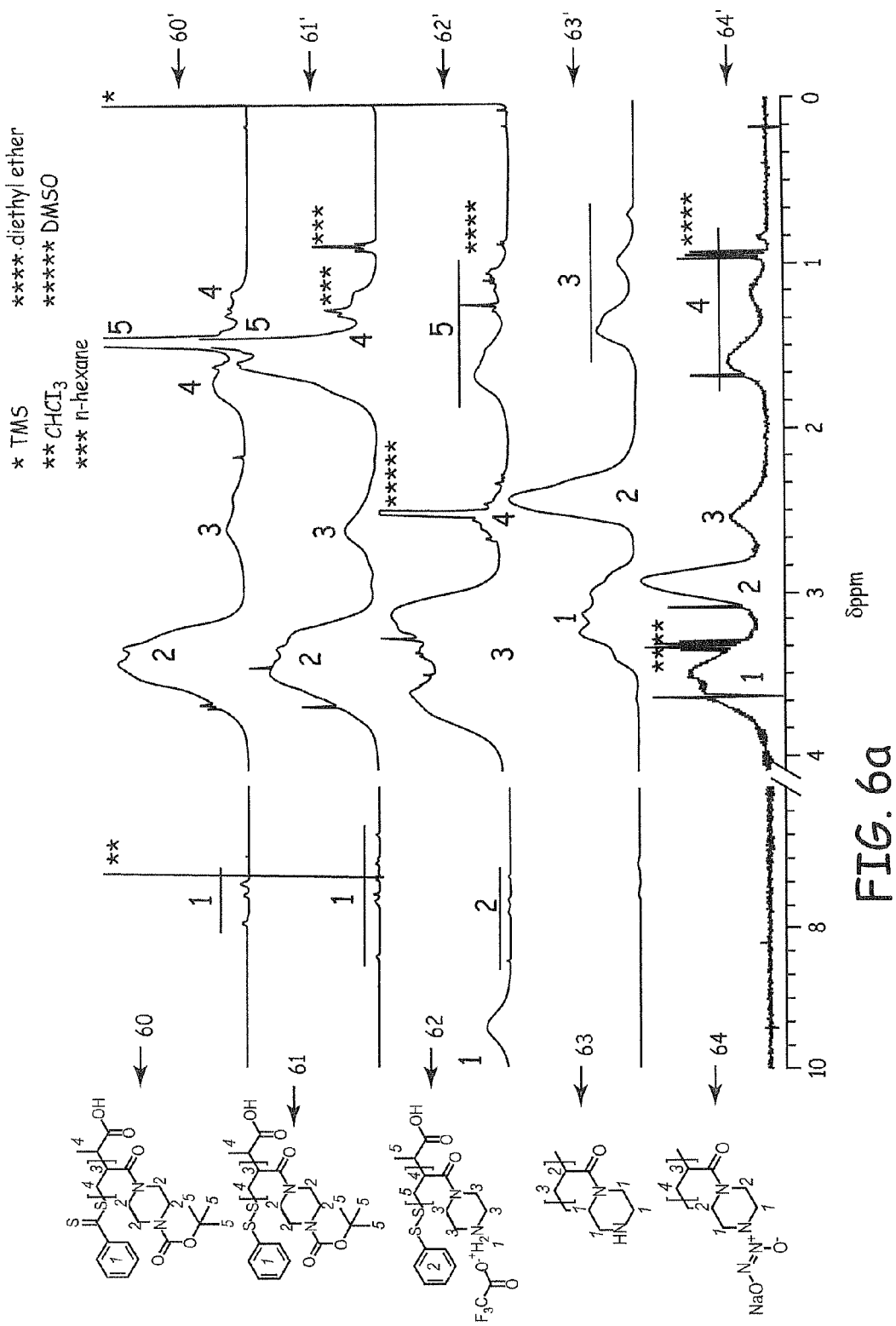
FIG. 6a shows 1H NMR (400 MHz) spectra 60', 61', 62', 63', 64', of PAZ series BocPAZ (60), BocPAZ-pyr (61), PAZ•TFA (62), PAZ (63), and PAZ•NONOate (64), respectively. As solvents, CDCl3 was used for BocPAZ (60) and BocPAZ-pyr (61). DMSO-d6 was used for PAZ-TFA (62). 0.1 M NaOD in D2O was used for PAZ (63) and PAZ•NONOate (64)
Figure 6B:
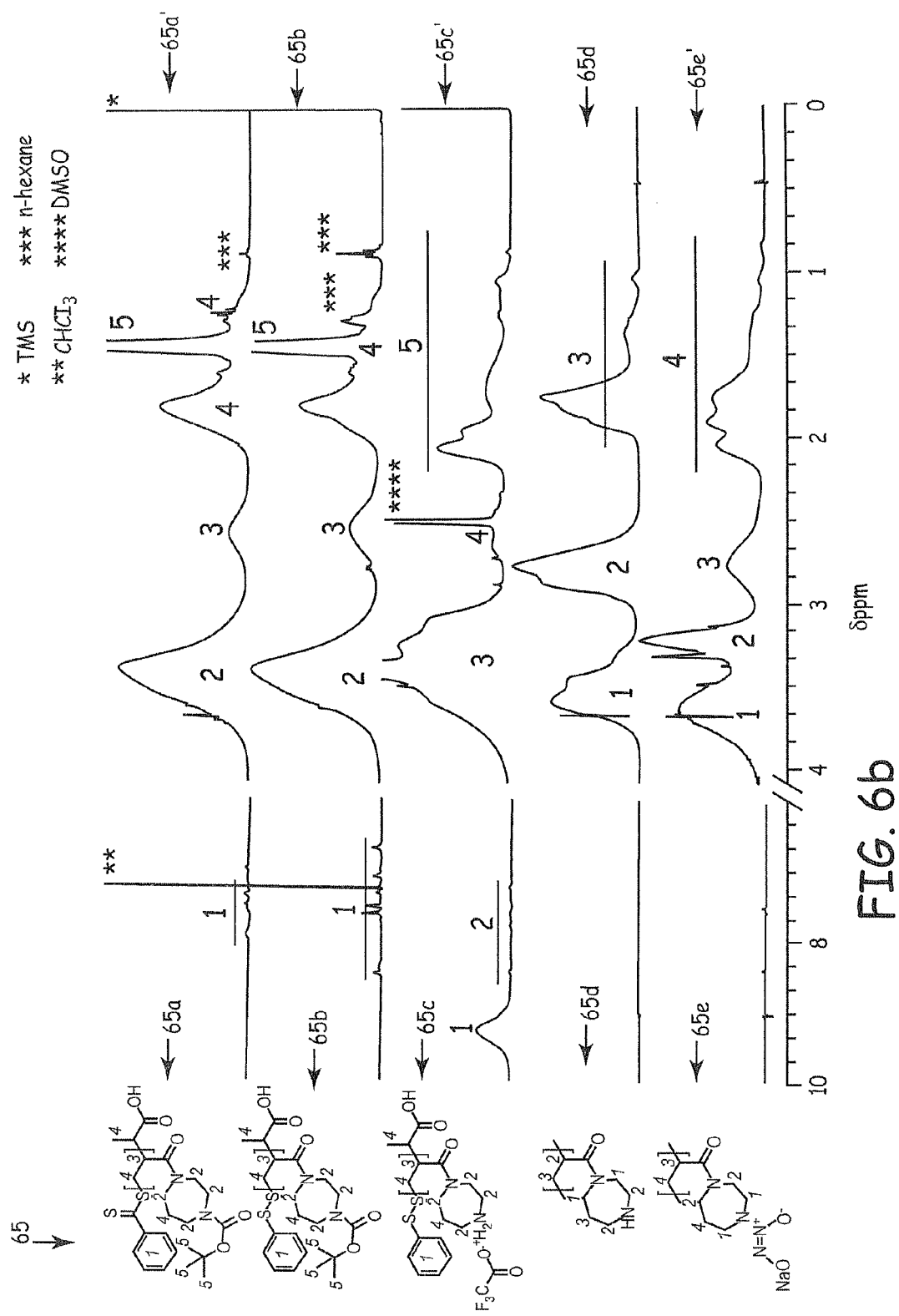
FIG. 6b shows 1H NMR (400 MHz) spectra (65a', 65b', 65c', 65d', 65e') of PAZh series 65: BocPAZh (65a), PAZh•TFA (65b), PAZh (65c), and PAZh•NONOate) (65d), respectively. As solvents, CDCl3 was used for BocPAZh (65a) and PAZh (65c). DMSO-d6 was used for PAZh•TFA (65b). 0.1 M NaOD in D2O was used for PAZh (65a) and PAZh•NONOate (65d)
Figure 6C:
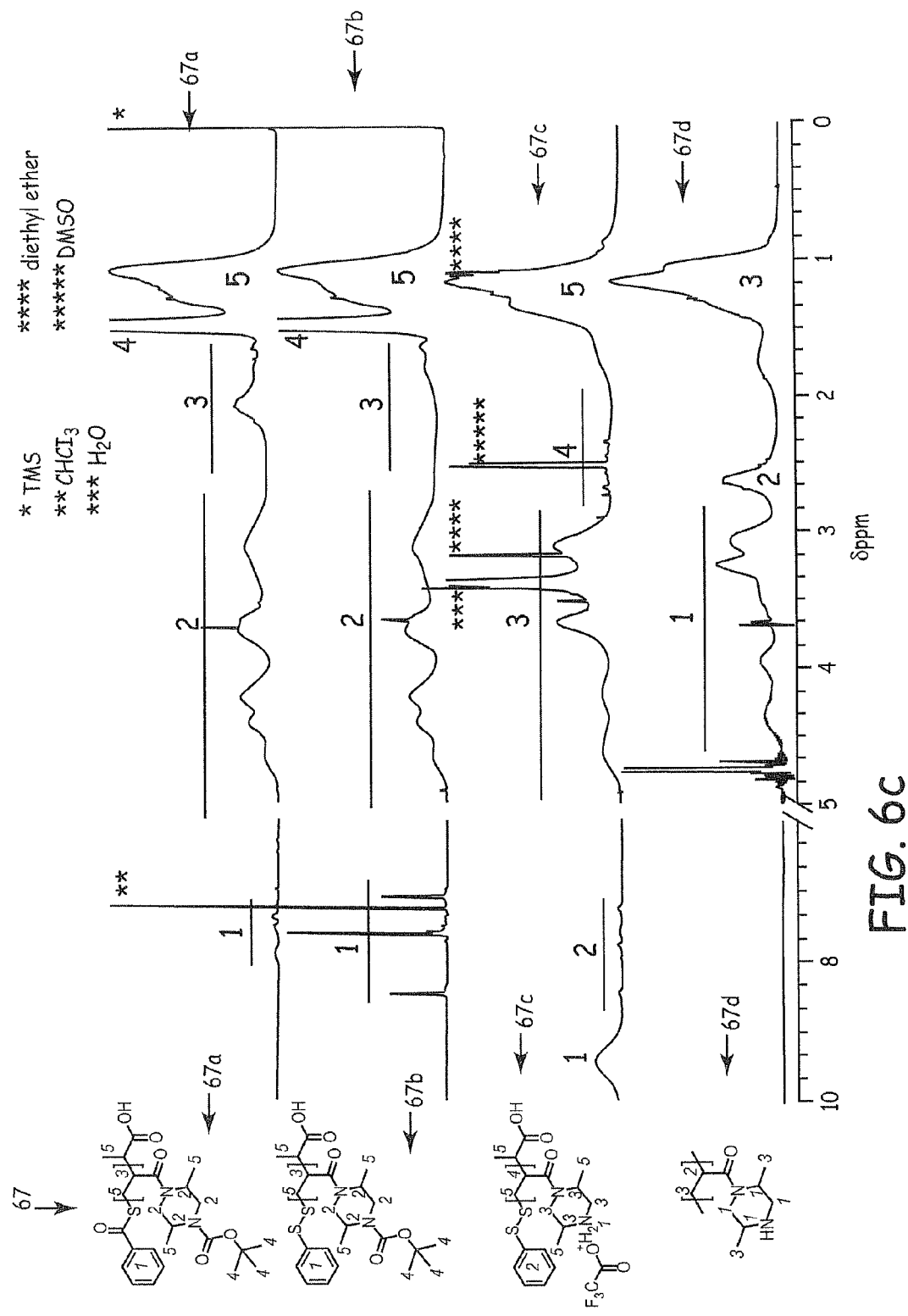
FIG. 6c shows 1H NMR (400 MHz) spectra (67a', 67b', 67c', 67d') of PAZd series 67 (from top, BocPAZd (67a), BocPAZd-pyr (67b), PAZd•TFA (67c), and PAZd (67d). As solvents, CDCl3 was used for BocPAZd (67a) and BocPAZd-pyr (67b). DMSO-d6 was used for PAZd•TFA (67c). 0.1 M NaOD in D2O was used for PAZd (67d)
Figure 6D:
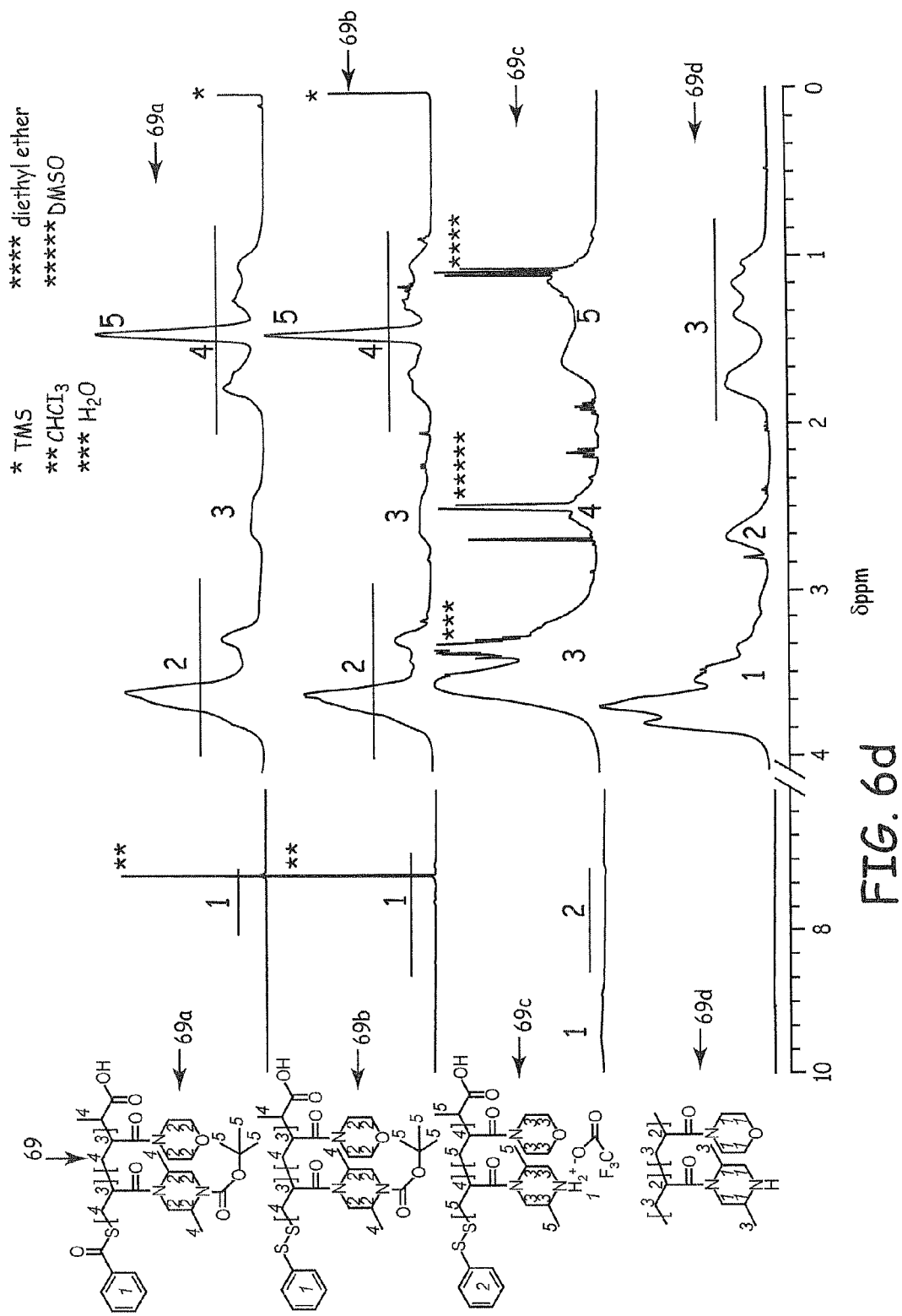
FIG. 6d shows 1H NMR (400 MHz) spectra of PAM-PAZd (69) series (from top, PAM-BocPAZd (69a), PAM-BocPAZd-pyr (69b), PAM-PAZd•TFA (69c), and PAM-PAZd (69d). As solvents, CDCl3 was used for PAM-BocPAZd (69a) and PAM-BocPAZd-pyr (69b). DMSO-d6 was used for PAM-PAZd•TFA (69c). 0.1 M NaOD in D2O was used for PAM-PAZd (69d)
Figure 7A:
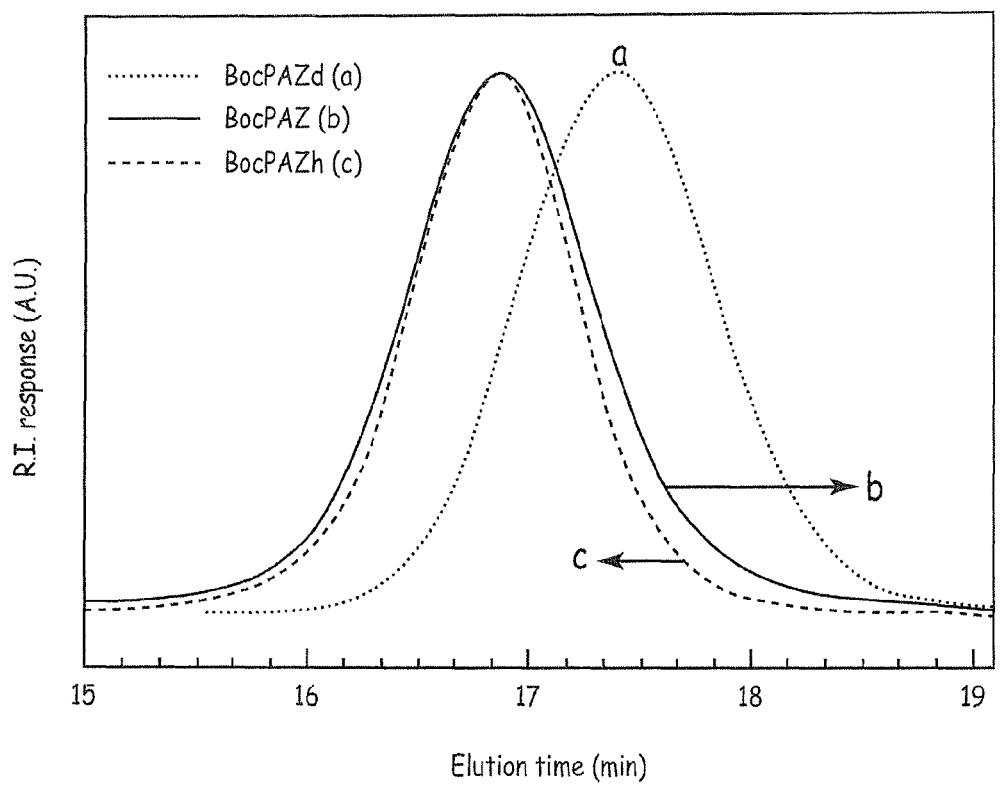
FIG. 7a shows SEC overlay for homopolymers.
Figure 7B:
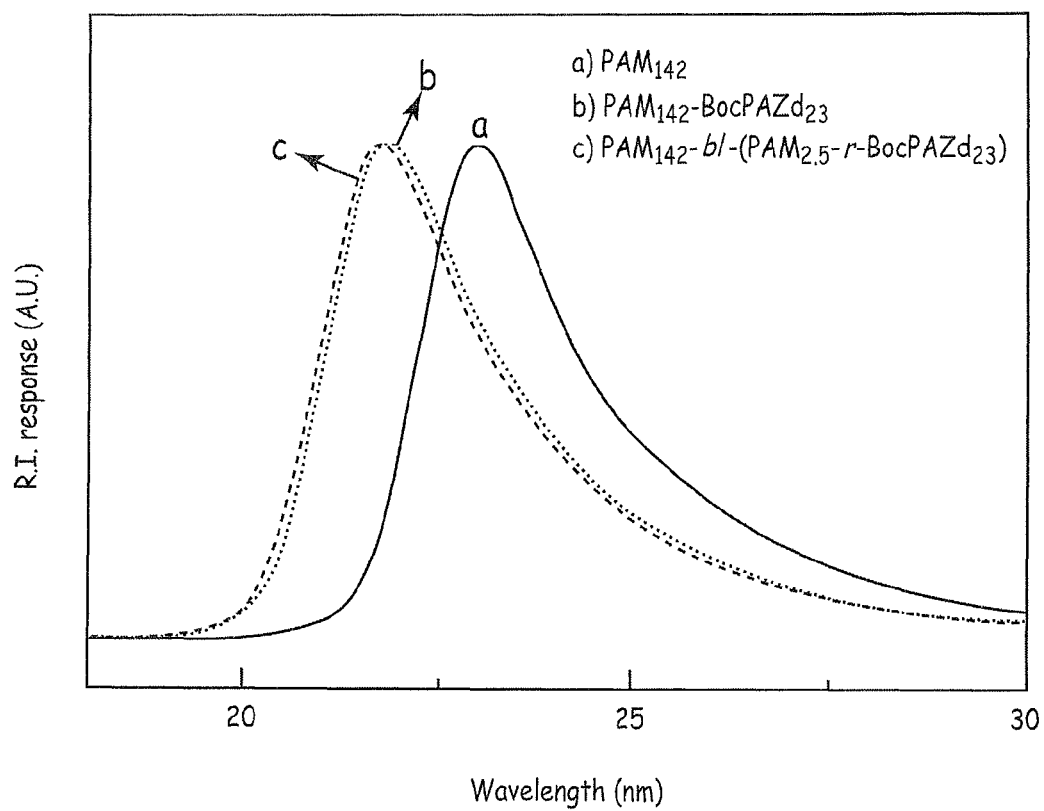
FIG. 7b shows SEC overlay for copolymer and terpolymers.
Figure 8:
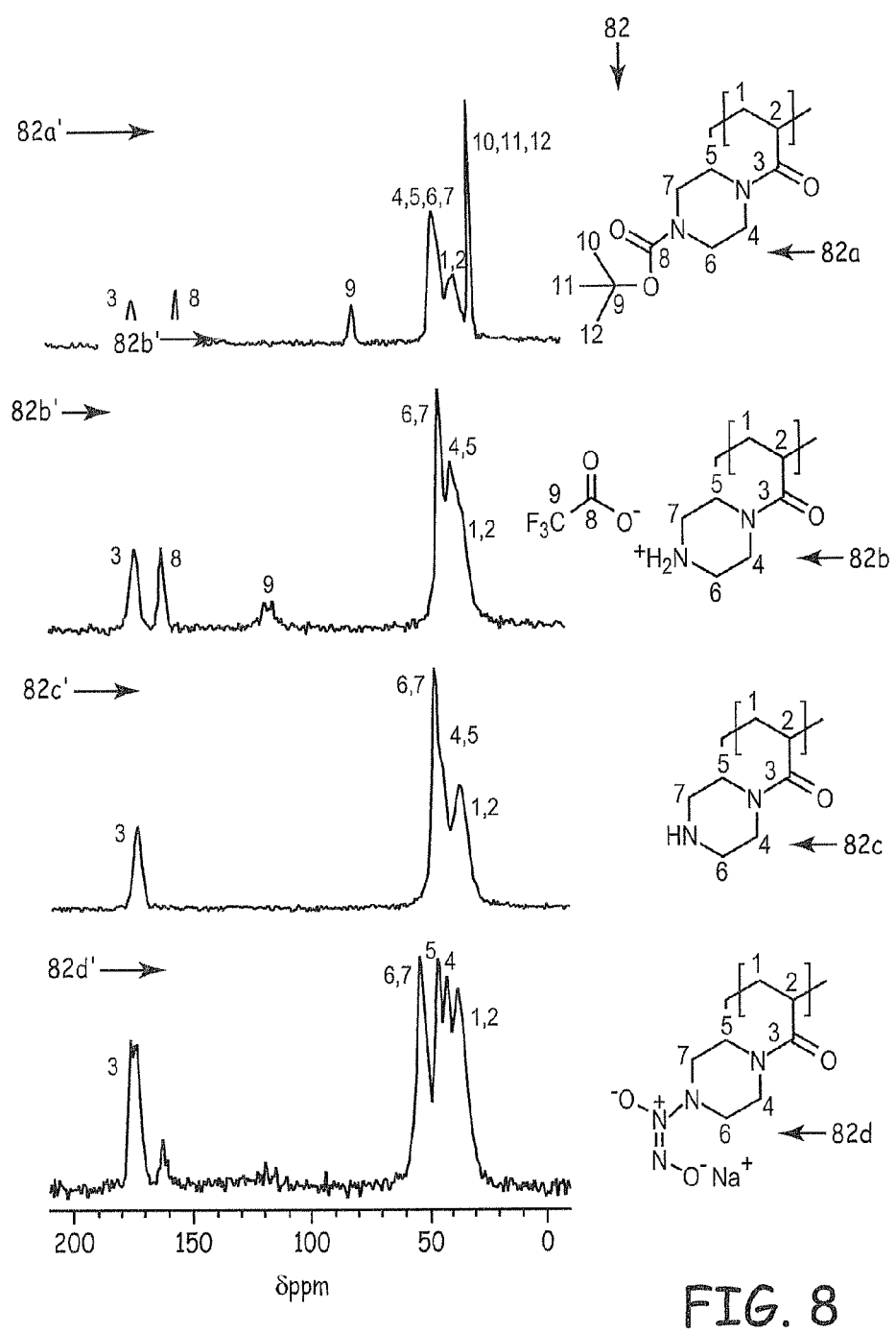
FIG. 8 shows $^{13}C\{^1H\}$ CPMAS NMR (75 MHz) spectra (82a', 82b', 82c', 82d') for PAZ series (82): from top, BocPAZ (82a), PAZ-TFA (82b), PAZ (82c), and PAZ•NONOate (82d), respectively.
Figure 9:
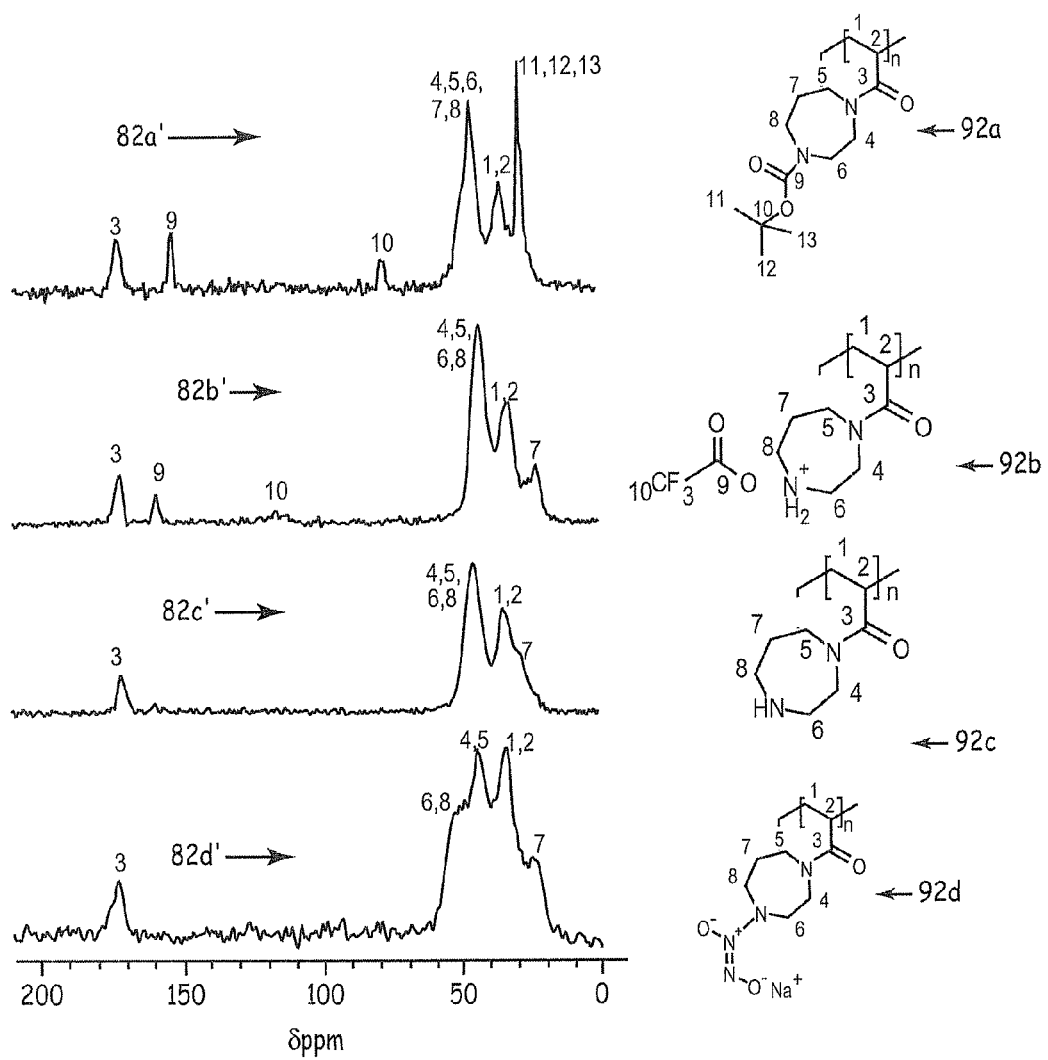
FIG. 9 shows $^{13}C\{^1H\}$ CPMAS NMR (75 MHz) spectra (92a', 92b', 92c', 92d', for PAZh series (92): From top, BocPAZh (92a), PAZh•TFA (92b), PAZh (92c), and PAZh•NONOate (92d), respectively.
Figure 10:
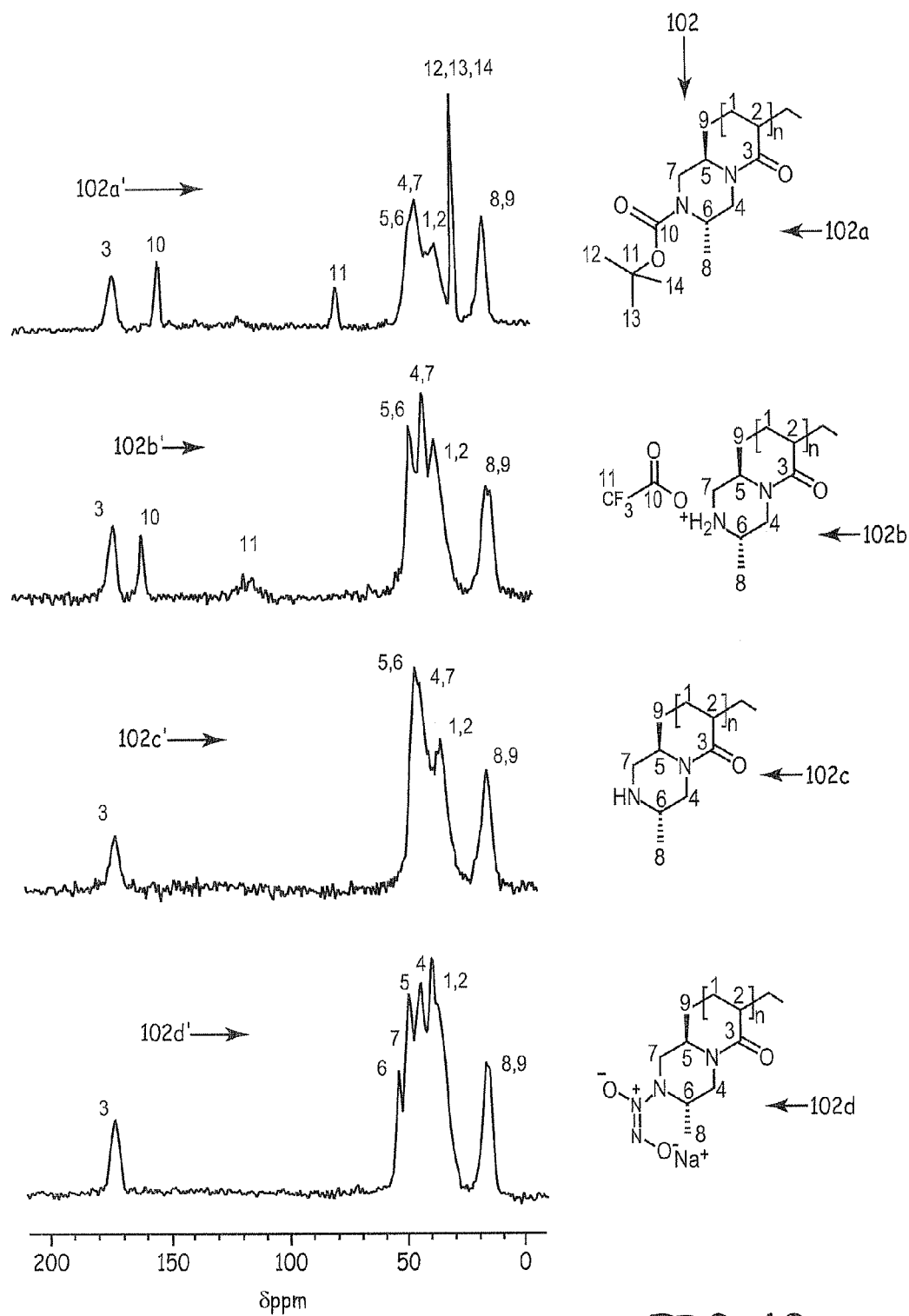
FIG. 10 shows $^{13}C\{^1H\}$ CPMAS NMR (75 MHz) spectra (102a', 102b', 102c', 102d') for PAZd series 102: From top, BocPAZd (102a), PAZdTFA (102b), PAZd (102c), and PAZd•NONOate (102d), respectively.
Figure 11:
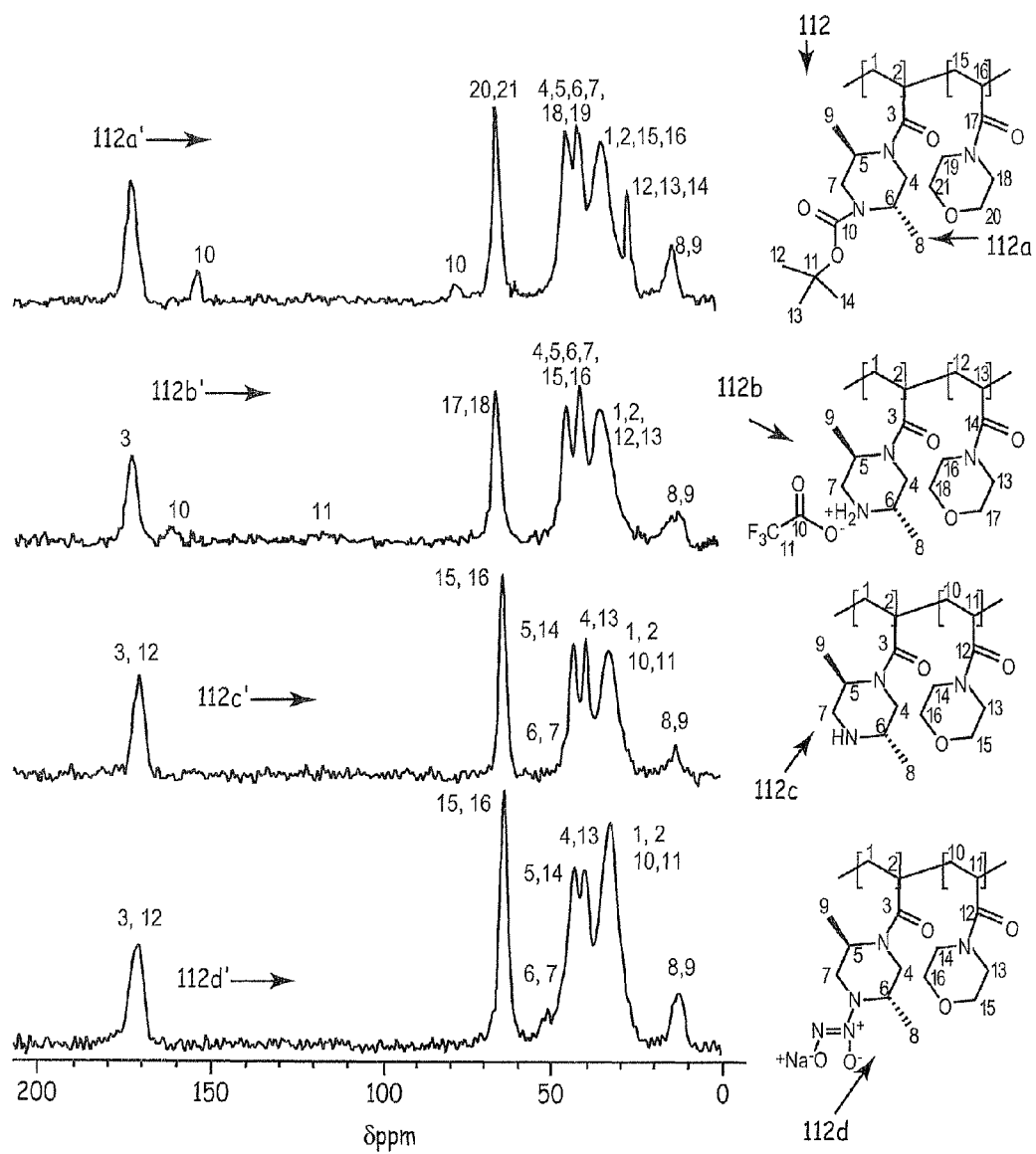
FIG. 11 shows $^{13}C\{^1H\}$ CPMAS NMR (75 MHz) spectra (112a', 112b', 112c', 112d') for PAM-PAZd series (112): From top, PAM-BocPAZd (112a), PAM-PAZd•TFA (112b), PAM-PAZd (112c), and PAM-PAZd•NONOate (112d)
Figure 12:
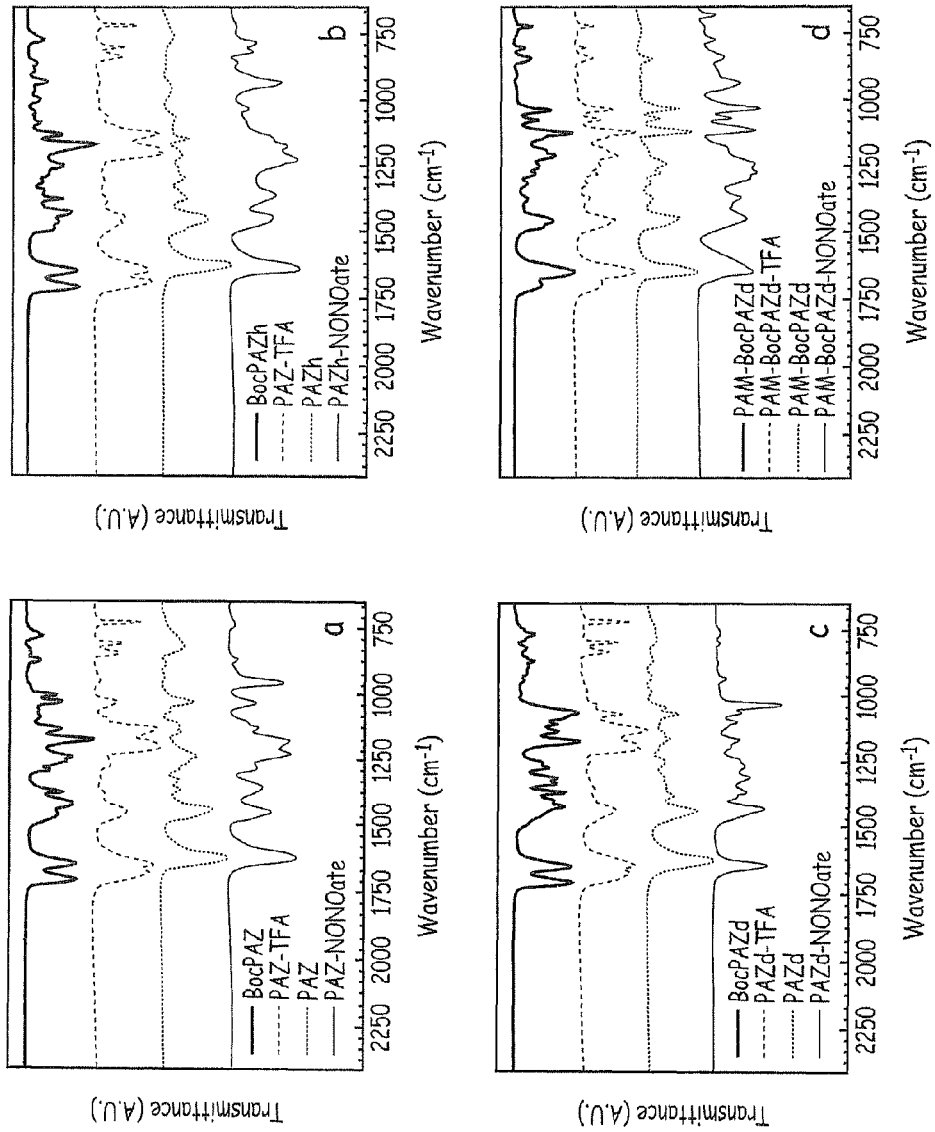
FIG. 12 shows FT-IR spectra of a) PAZ series, b) PAZh series, c) PAZd series, and d) PAM-PAZd series.

Finally, how micelles can be distributed in a dense tissue such as the arterial media was examined by ex vivo infusion into rabbit carotid artery. Freshly harvested rabbit carotid arteries were used without injury to the endothelium. With respect to the size effect in arterial infusion, Westedt et al. showed that particles with around 100 nm of diameter easily penetrated through the intima and remained in the media, while micron-sized beads were too large to penetrate the intima and media[26,27]. As for ex vivo infusion, two different conditions are employed: static infusion for 1 min and pulsed infusion for 10 sec repeated 10 times. The transmural pressure was maintained at 1 atm in both cases. Comparing the static infusion to the pulsed infusion, as seen in FIG. 4, the polymer micelles were readily delivered to the media, with more being delivered with the pulsed protocol[27]. Referring to FIG. 4, Poly[(N-acryloylmorpholine)-bl(sodium 1-[4-acryloyl-2,5-dimethylpiperazin-1-yl]diazen-1-ium-1,2-diolate)] (PAM-PAZd•NONOate) were infused ex vivo and shown to penetrate the arterial intima and media. Fluorescence microscopy images were taken from rabbit carotid artery after ex vivo infusion of coumarin-labeled $PAM_{146}$-PAZd•NONOate$_{23}$ micelles. Images from FIG. 4A panel a to panel c represent the artery infused under static conditions (1 atm for 1 min). Images from part FIG. 4A panel d to panel f represent the pulsed condition (1 atm for 10 s repeated 10 times). Images of FIG. 4A panel b and FIG. 4A panel d were from auto-fluorescent elastin in the artery. Images of FIG. 4A panel c and FIG. 4A panel e were from coumarin-labeled $PAM_{146}$-PAZd•NONOate$_{23}$ micelles. Images of FIG. 4A panel a and FIG. 4A panel c are merged with the signals from auto-fluorescent elastin and coumarin-labeled micelles infused. The graph in FIG. 4B represents the distribution of the coumarin-labeled micelles across the rabbit carotid artery. The intensity values are an average of 4 different places from the images. The intensity of fluorescence was calculated by processing METAMORPH imaging systems.

Many particulate NO donors have been developed by others: poly(ethylene imine) (PEI)-based microspheres[28], poly (methylmethacrylate) (PMMA)-based microbeads[6], and N-diazeniumdiolate (NONOate)-modified silica microparticles[4] and gold nanoparticles[3] are just a few examples. Despite such examples in the aforementioned works, the size of polymeric particles is mostly in a micron-regime, in case of silica[4], PMMA[6] and PEI microparticles28, and/or the release rate of NO is extremely fast in most case of nanoparticles[3]. There are examples of NO-releasing materials which do so over the course of a long time span, especially in hydrogel forms[29], for example based on primary amine complexes; it is, however, well known that primary amines form very unstable NONOates upon reaction with NO gas[30].

Differently from cases cited above, herein is presented a polymer chemistry and physicochemical response in which NONOation drives micellization of a soluble diblock copolymer comprising a poly(secondary amine) domain. Careful selection of the solubility of the poly(secondary amine) allowed it to be soluble in the native state but insoluble in water as the NONOate, this difference driving micellization and the hydrophobic core restricting access to protons required for NO generation. The slow influx of protons provides a slow liberation of NO and a slow solubilization of the micelle to the native, soluble polymer. Advantageously, herein are provided either soluble or nanoscopic NO delivery forms, since NO after liberation from the NONOate is extremely unstable and thus only locally active.

While it is demonstrated herein that distribution throughout the arterial media is possible, in the context of post-PTCA restenosis prevention, other applications, such as, such as for accelerating wound-healing[29] or preventing post-operational abdominal adhesion formation[31] are possible.

The micelles may be prepared in advance and stored prior to use, or prepared at about the time of a patient procedure (e.g., immediately before, after the start of the procedure, in the operating room). One method of preparation is to prepare suitable polymers as described herein, dissolve them in a suitable solvent, e.g., aqueous solvent (e.g., water) to form micelles spontaneously. The formation may be achieved substantially without external energy (e.g., without mechanical energy, without heat, or without mechanical energy and without heat), or with the application of external mechanical energy (e.g., shaking by hand, vibrating with a mechanical device, mixing with a mechanical mixer (rotating rapidly, e.g., a VORTEX device), or stirring). Heat may optionally be applied, e.g., warming to about physiological temperature (about 37° C.).

Accordingly, some embodiments relate to a kit with components for preparing and/or delivering micelles. A kit refers to a collection of materials needed by a user to accomplish the intended task; the kit may be provided, for instance, in a unitary housing such as a box, envelope, or package. Instructions to prepare the materials to make micelles may include steps as needed to guide the user, e.g., as described elsewhere herein. An applicator may be provided in the kit or separately. Examples of applicators are syringes, swabs, or wipes.

Micelles may be provided to the patient topically or internally. Topical application involves noninvasively placing a collection of micelles in contact with a tissue of the patient, e.g., on the skin, buccaly, or by suppository.

One method of application relates to applying pressure to force a collection of micelles into a patient, usually across a tissue, e.g., skin, vascular lumen, or organ tissue. One method of creating such pressure is to prepare the micelles in a bandage that is adhered to a tissue of the patient, such that force applied to the patch creates pressure inside the bandage that forces the micelles into the tissue. One bandage embodiment is a bandage with a nonpermeable backing rimmed with adhesive or a sealing gasket that holds the pressure applied to the backing material without allowing escape of the bandage contents (micelles) around the bandage. The pressure may be applied for, e.g., 5 seconds to a month, either manually or by use of a compression aid. In the case of the bandage embodiment, a tightly fitting sleeve or wrapping may be used to create a desired amount of compression to provide the desired pressure.

Pressure across a tissue surface may also be created internally, e.g., in minimally invasive procedures for placing a medical device in a patient. In the context of Percutaneous Transluminal Coronary Angioplasty (PTCA), one embodiment uses occlusive balloons that block a lumen of a blood vessel or organ (e.g., at least one heart chamber) when a collection of micelles is delivered (e.g., in a pharmaceutically acceptable carrier), with the user introducing the carrier into the lumen and applying pressure against the balloon to force the carrier and micelles into the tissue. Alternatively, at least a portion of a stent may be coated with the micelles, with the micelles being released from the coating into a tissue adjacent or near the stent.

FIG. 15A depicts a catheter comprising a plurality of occlusive balloons for delivering a fluid with the micelles or other materials described herein. Catheter 150 has openings 152, 154 for inflating balloons 156,158, respectively, via conduit 160 to force the balloons against tissue 161 of lumen 162. Fluid indicated by arrow A is introduced to carry micelles in a suitable diluent into the catheter, which it exits via holes 164 as indicated by arrows B. The user applies pressure to force the micelles into tissue 161. Examples of pressure and times are: exposure for up to 1 min at up to 2 atm; higher application pressures are possible, but in general lower pressures and lower times are beneficial and are effective because the micelles are small.

FIG. 15B depicts a catheter system comprising an occlusive balloon on a catheter and a second occlusive balloon on a guidewire for delivering a fluid with the micelles or other materials described herein. Catheter 170 has an opening (not shown) for inflating balloon 172 via a conduit (not shown) to force balloon 172 against tissue 174 of lumen 176. Fluid indicated by arrow A is introduced to carry micelles in a suitable diluent into the catheter, which it exits via opening 178 as indicated by arrows A. Balloon 180 in the inflated position blocks lumen 176 after inflation through guidewire 182. The user applies pressure through catheter 170 to force the micelles into tissue 174, e.g., using times and pressures as already indicated.

Alternatively other catheter-based systems may be used to introduce a fluid comprising a collection of micelles, e.g., as in U.S. Pat. Nos. 5,295,962, 5,421,826, 5,423,745, 5,833,658, 6,720,350, 6,764,461, or 7,303,574, which are hereby incorporated by reference herein to the extent they do not contradict what is disclosed herein.

Micelles may be delivered as coatings. Micelle formulations can be formed in water, spray-coated on material surfaces, and dried on those surfaces. Other excipients can be incorporated into the spraying solution or suspension to enhance drying, re-dissolution once placed in the body, or retention of micellar structure after re-dissolution after placement in the body. Such surfaces can be the surfaces of implantable devices, such as coronary artery stents, or of temporarily-placed devices, such as the surfaces of drug delivery catheters.

Pharmaceutically acceptable carriers or excipients may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a pharmaceutically acceptable carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in this arts. Residual amines may be complexed with sodium, potassium, or a other suitable counter-ions. Thus a pharmaceutically acceptable composition has a carrier, salt, or excipient suited to administration to a patient. Moreover, inert components of such compositions are biocompatible and not toxic.

The micelles or polymers described herein may be administered in admixture with suitable pharmaceutical diluents, solutions, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

In use, micelles may be provided to a patient by a method comprising introducing to the patient, e.g., by injection, orally, buccaly, as a suppository, transdermally, transdermal patch, or topically, e.g., by ointment or salve. Introducing the micelles to the patient in some embodiments comprises delivering the micelles across a tissue surface of a patient under pressure. Other embodiments relate to using the micelles in a coating. The micelles can be mixed, suspended, dissolved, and/or dispersed in the coating. Hydrophilic coatings made with polymers that are at least slightly water soluble can allow for diffusion of the micelles through the coating. Or degradation of the coating may alternatively release, or enhance release, or the micelles.

Materials and Methods

Monomer syntheses. N-acryloylmorpholine was synthesized as described elsewhere[19]. 1-Boc-4-acryloylpiperazine, 1-Boc-4-acryloylhomopipereazine, and 1-Boc-4-acryloyl-2,5-dimethylpiperazine were synthesized as described elsewhere[32] with modifications. N-acryloylmorpholine, 1-Boc-4-acryloylpiperazine, and 1-Boc-4-acryloylhomopipereazine were purified with repeated acid/base washing. 1-Boc-4-acryloyl-2,5-dimethylpiperazine was purified with column chromatography.

Polymer syntheses. Homo- and co-polymerization were carried out as described elsewhere[19]. Boc-protected polymers were deprotected with a TFA/$CH_2Cl_2$ mixture overnight. By basifying with $CH_3ONa$, deprotonated polyamine was dialyzed to remove TFA•Na salt and lyophilized. Poly(NONOate)s were synthesized with NO gas under 80-150 psi for 5 d. in situ micelle formation. PAM-PAZd•NONOate was dissolved in MILLI-Q water with $CH_3ONa$. After degassing with Ar for 1 hr, NO was pressurized to 80-150 psi in an autoclaving vessel. This reaction was continued for 5 d.

NO analysis. At 25° C., dissociation of NONOate in PBS (10 mM, pH 7.4) was monitored by UV spectrometry at 250 nm. At 37° C., NO radicals generated from poly(NONOate)s in PBS (10 mM, pH 7.4) were recorded by a NO analyzer.

Labelling micelles with florescence. In a PAM-PAZd•NONOate micellar suspension, sulfo-N-hydrxysuccinimide (sulfo-NHS) and N-(3-dimethylaminopropyl)-N'-ethylcarbodiimide hydrochloride (EDC) were mixed to activate carboxylic acid groups on the surface of micelles. High excess amounts of 2,2'-ethylenedioxy)diethylamine (EDDA) was reacted overnight. After removing unreacted EDDA by dialysis, methanol containing 7-hydroxycoumarin-3-carboxylic acid N-succinimidyl ester (hydroxycoumarin-NHS) was added dropwise to the amine-functionalized micelle suspension. The sample was dialyzed for 2 d under darkness, and unreacted hydroxycoumarin-NHS was removed by centrifugation. To remove it more excessively, additional dialysis was performed overnight.

ex vivo infusion of micelles in the rabbit carotid artery. Carotid arteries from male New Zealand white rabbits weighing 3 to 3.5 kg were obtained from a local slaughterhouse immediately upon sacrifice. Vessels were stored in a PBS solution and put on ice for transport. Excess tissue and adventitia were removed, and a 2 cm-long arterial segment was mounted on 2.5 mm diameter cannula. The arteries were then stretched longitudinally to their in vivo length, submerged in a Krebs buffer solution and kept at 37° C. for 1 h. Following this, a Krebs solution filling the artery was replaced by approximately 1 mL of fluorescent-labelled micelle solution. A Millar MIKRO-TIP catheter transducer was inserted through one cannula while a 20 mL syringe full of air was attached to the other cannula. Experimental conditions were achieved by depressing the plunger of the syringe and fixing the transmural pressure at 1 atm (for 1 min) or repeatedly depressing and releasing the plunger of the syringe, creating a pulsating pressure ranging from ambient to 1 atm every 10 s (×10). After the experiment the artery was rinsed for one minute in Krebs solution, fixed in tissue freezing medium (TISSURE-TEK O.C.T.) and kept at −20° C.

1. Materials 1.1. Chemicals

Chemicals were used as received unless stated otherwise. Sodium methoxide solution (0.5 M in methanol), trans-2,5-dimethylpiperazine (98%), 2,2'-dithiodipyridine (98%), n-hexylamine (99%), 2-bromopropionic acid (99+%), phenylmagnesium chloride (2.0 M in THF), carbon disulfide (99+%), $Na_2SO_4$ (99%), and $NaHCO_3$ (99.5%) were purchased from Sigma-Aldrich (Steinheim, Germany). Morpholine (99+%), piperazine (anhydrous, 98%), homopiperazine (98%), AIBN (98+%), di-tert-butyldicarbonate (99.5%), citric acid (98%), $KMnO_4$ (99+%), $CaH_2$ (95+%), $K_2CO_3$ (99+%), $KHSO_4$ (98+%), ninhydrin (99%), LiAlH4 (97+%), and acryloyl chloride (96+%) were purchased from Fluka (Buchs, Switzerland). AIBN was recrystallized from methanol. Trifluoroacetic acid (TFA) (99%), sodium borate decahydrate (ACS reagent grade), triethylamine (TEA) (99%), and boric acid (99+%) was purchased from Acros (Geel, Belgium). Tris(hydroxymethyl aminomethane) was purchased from Biosolve B.V. (Valkenswaards, the Netherlands). TEA was distilled over $CaH_2$ and ninhydrin, and stored over dried molecular sieves until used.

1.2. Solvents and Buffers

Diethyl ether, n-hexane, dichloromethane ($CH_2Cl_2$), chloroform ($CHCl_3$), and toluene were purchased from VWR (Dietikon, Switzerland) in reagent grade. 1,4-Dioxane (Fluka) was distilled over $LiAlH_4$ and stored over molecular sieves until used. THF, diethyl ether, and methanol were purchased from Acros in HPLC grade. Ethyl acetate was purchased from Merck KGaA (Darmstadt, Germany) in reagent grade. Bi-distilled water or Milli-Q water was used for dialysis. Phosphate buffered saline (PBS, $Ca^{2+}/Mg^{2+}$ free)

was purchased from Gibco (Paisley, UK). Other buffers (10 mM commonly); acetate for acidic buffer, phosphate for neutral buffer, Tris and borate for basic buffer) were prepared in Milli-Q water according to the standard protocol.

1.3. NMR Chemicals

NMR solvents ($CDCl_3$, DMSO-$d_6$) and tetramethylsilane (TMS) were purchased from Armar chemicals (99.8%, Döttingen, Switzerland). 40% NaOD in $D_2O$ was purchased from Dr. Glaser AG (Basel Switzerland). Deuterium oxide ($D_2O$, 99.9% atom % D) was purchased from Sigmna-Aldrich.

1.4. Gases and High Pressure Reaction Apparatus

Ar gas was passed over anhydrous $CaSO_4$ to remove water. Nitric oxide (NO) was purchased from Messer Schweiz AG (Preverenges, Switzerland). Reactions with NO were carried out in a 4790 stainless steel high pressure reactor (Parr Inst., Moline, USA) with a Teflon beaker insert. The reactor was connected to Ar gas (Messer Schweiz AG) in order to purge the reactor before filling with NO gas. Pressure was measured with a gage block assembly (working range: 0-200 psi).

1.5. Miscellaneous

Regenerated cellulose membranes were purchased from Spectrapor (Breda, the Netherlands).

2. Characterization and Analysis

All the details regarding purification by column chromatography, thin layer chromatography (TLC), solution $^1H$ NMR spectra, solid state $^{13}C\{^1H\}$ CPMAS NMR spectra, size exclusion chromatography (SEC), and UV/vis measurements can be found elsewhere[33]. Fourier transform infrared (FT-IR) spectra were recorded as thin films in ATR mode on a Perkin-Elmer Spectrum One spectrometer and band positions are given in $cm^{-1}$. Elemental analysis was done by the Institute of Chemical Sciences and Engineering (ISIC) at EPFL, Switzerland. Mass spectra were obtained using Waters Micromass ZQ instrument with ESI+ (capillary voltage: 3.0 kV) or APCI+ (corona current: 8.0 μA) ionization modes.

3. Synthesis 3.1. Monomer Synthesis

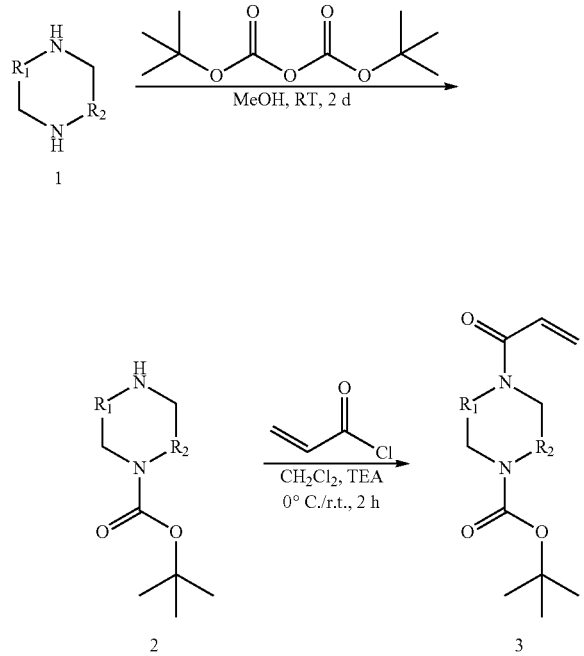

Scheme 1. Monomer synthesis a: $R_1 = CH_2$, $R_2 = CH_2$
b: $R_1 = CH_2CH_2$, $R_2 = CH_2$
c: $R_1 = CH_3CH$, $R_2 = CH_3CH$ 3.1.1. Mono-Protected Amines The synthesis procedures were referred to as reported by Zheng et al[32]. To prepare tert-butoxycarboxylic (Boc) protected amine, a solution of di-tert-butyl dicarbonate (7.60 g, 0.035 mol) solution in 65 mL of MeOH was added drop-wise to a solution of 0.063 mol of respective amine in 140 mL of MeOH previously cooled at 0° C. After 25 min, all di-tert-butyl dicarbonate had been added and the mixture was warmed to room temperature. After 2 d, the solution was concentrated under reduced pressure and the white residue dissolved in 200 mL of $Et_2O$. The aqueous solution obtained by extracting the organic solution with 1 M citric acid (aq) (3×100 mL) was washed with EtOAc (3×100 mL) and brought to pH=11 by adding solid $K_2CO_3$. The turbid solution was extracted with EtOAc (3×100 mL) and dried over $Na_2SO_4$. The solution was concentrated under reduced pressure at 40° C. and stripped with $CH_2Cl_2$ to yield clear oil which was crystallized into a white solid (2a, 2c) or yellowish oil (2b) upon drying under reduced pressure. As for 1-Boc-2,5-dimethylpiperazine (BocZd, 2c), column chromatography ($SiO_2$, MeOH) was performed to separate the product from any unsubstituted diamine.

1-Boc-piperazine (BocZ, 2a) Yield: 71%; TLC (MeOH): $R_f$=0.30; $^1H$ NMR (400 MHz, $CDCl_3$) δ 3.45-3.33 (m, 4H, N—$CH_2$), 2.88-2.74 (m, 4H, NH—$CH_2$), 1.57 (s, 1H, NH), 1.46 (s, 9H, C($CH_3$)$_3$); Anal. Calcd. for $C_9H_{18}N_2O_2$: C, 58.04; H, 9.74; N, 15.04. Found: C, 57.38; H, 9.56; N, 14.82; MS (m/z, M+H$^+$, APCI+): 186.3. 1-Boc-homopiperazine (BocZh, 2b) Yield: 38%; TLC (MeOH): $R_f$=0.30; $^1H$ NMR (400 MHz, $CDCl_3$) δ 3.61-3.41 (m, 4H, N—$CH_2$), 3.06-2.78 (m, 4H, NH—$CH_2$), 1.83 (td, 2H, $CH_2$), 1.68 (s, 1H, NH), 1.52 (s, 9H, C($CH_3$)$_3$); Anal. Calcd. for $C_{10}H_{20}N_2O_2$: C, 59.97; H, 10.07; N, 13.99. Found: C, 57.47; H, 11.58; N, 13.99; MS (m/z, M+H$^+$, APCI+): 200.3. 1-Boc-2,5-dimethylpiperazine (BocZd, 2c) Yield: 18%; TLC (MeOH): $R_f$=0.26; $^1H$ NMR (400 MHz, $CDCl_3$) δ 4.19-4.03 (s, 1H, N—CH), 3.53 (td, 1H, NH—CH), 3.28-3.16 (m, 2H, N—$CH_2$), 3.16-3.04, 2.47 (m, 2H, NH—$CH_2$), 1.73-1.56 (s, 1H, NH), 1.45 (s, 9H, C($CH_3$)$_3$), 1.18 (m, 6H, CH—$CH_3$;. Anal. Calcd. for $C_{11}H_{22}N_2O_2$; C, 61.65; H, 10.35; N, 13.07. Found: C, 59.36; H, 10.53; N, 12.95; MS (m/z, M+H$^+$, APCI+): 214.3.

3.1.2. Acylation of Mono-Protected Amines

A solution of 831 μL acryloyl chloride (0.01 mol) in 10 mL of $CH_2Cl_2$ was added to a solution of 9.0×10$^{-3}$ mol of respective mono-protected amine (2a, 2b, 2c) and 1.25 mL of TEA (9.0×10$^{-3}$ mol) in 50 mL of $CH_2Cl_2$ previously cooled at 0° C. After 10 min, all acryloyl chloride had been added and the mixture was warmed to room temperature. After 2 h, the clear solution was washed with $H_2O$ (100 mL), 1 M $KHSO_4$ (aq) (100 mL), $H_2O$ (100 mL), 5% $NaHCO_3$ (aq) (100 mL), and $H_2O$ (100 mL). The clear solution was dried over $Na_2SO_4$, and concentrated under reduced pressure at 30° C. to yield clear colorless oil that solidified to a white solid (3a, 3c) or yellowish oil (3b). The monomer was obtained with purity higher than 95% and showed negative reaction by ninhydrin. Once synthesized the monomer was protected from light and kept at −20° C. prior to polymerization.

1-Boc-4-acryloylpiperazine (AZ, 3a) Yield: 95%; TLC (EtOAc): $R_f$=0.38; $^1$H NMR: δ=6.56 (dd, 1H, CH=CH$_2$), 6.31 (dd, 1H, CH=CH$_{trans}$), 5.73 (dd, 1H, CH=CH$_{cis}$), 3.74-3.37 (m, 8H, CH$_2$), 1.48 (s, 9H, C(CH$_3$)$_3$); Anal. Calcd. for C$_{12}$H$_{20}$N$_2$O$_3$: C, 59.98; H, 8.39; N, 11.66. Found: C, 59.34; H, 8.76; N, 11.42; MS (m/z, M+H$^+$, APCI+): 241.2.

1-Boc-4-acryloylhomopiperazine (AZh, 3b) Yield: 97%; TLC (EtOAc): $R_f$=0.30; $^1$H NMR (400 MHz, CDCl$_3$) δ 6.58 (dd, 1H, CH=CH$_2$), 6.48-6.17 (m, 1H, CH=CH$_{trans}$), 5.69 (t, 1H, CH=CH$_{cis}$), 3.76-3.22 (m, 8H, N—CH$_2$), 2.03-1.75 (m, 2H, CH$_2$—CH$_2$—CH$_2$), 1.45 (s, 9H, C—(CH$_3$)$_3$); Anal. Calcd. for C$_{13}$H$_{22}$N$_2$O$_3$: C, 61.39; H, 8.72; N, 11.01; O. Found: C, 59.33; H, 10.36; N, 11.03; MS (m/z, M+H$^+$, APCI+): 254.2.

1-Boc-4-acryloyl-2,5-dimethylpiperazine (AZd, 3c) Yield: 94%; TLC (EtOAc): $R_f$=0.45; $^1$H NMR (400 MHz, CDCl$_3$) δ 6.67-6.39 (ddd, 1H, CH=CH$_2$), 6.39-6.24 (m, 1H, CH=CH$_{trans}$), 5.79-5.60 (td, 1H, CH=CH$_{cis}$), 4.98-3.98 (m, 2H, N—CH), 3.94-2.92 (m, 4H, N—CH$_2$), 1.46 (s, 9H, C—(CH$_3$)$_3$), 1.36-0.94 (m, 6H, CH—CH$_3$); Anal. Calcd. for C$_{14}$H$_{24}$N$_2$O$_3$: C, 62.66; H, 9.01; N, 10.44. Found: C, 61.86; H, 9.04; N, 10.23; MS (m/z, M+H$^+$, APCI+): 268.2.

3.2. Homopolymerizations

Scheme 2. Homopolymerization and end group modification by aminolysis and substitution with 2,2'-dithiodipyridine.

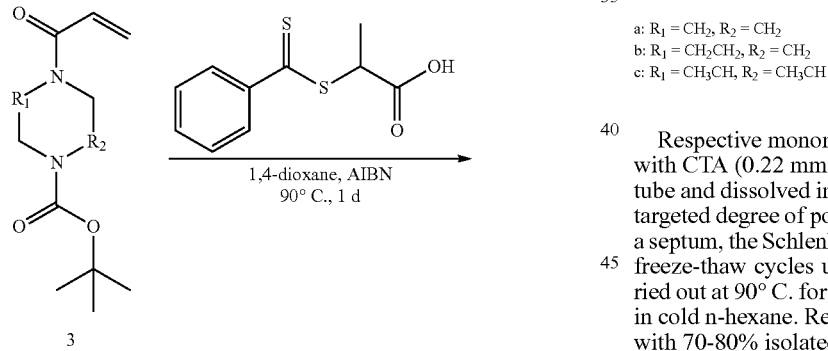

a: $R_1$ = CH$_2$, $R_2$ = CH$_2$
b: $R_1$ = CH$_2$CH$_2$, $R_2$ = CH$_2$
c: $R_1$ = CH$_3$CH, $R_2$ = CH$_3$CH

Respective monomer (3a, 3b, 3c) (10.8 mmol) was loaded with CTA (0.22 mmol) and AIBN (0.02 mmol) in a Schlenk tube and dissolved in dioxane with 1.6 M concentration. The targeted degree of polymerization was 50. After closing with a septum, the Schlenk tube was purged with Ar following five freeze-thaw cycles under vacuum. Polymerization was carried out at 90° C. for 24 h and the polymers were precipitated in cold n-hexane. Resulted polymers (4a-4c) were recovered with 70-80% isolated yields.

3.3. Diblock Copolymerization

Scheme 3. Diblock copolymerization and end group modification by aminolysis and substitution with 2,2'-dithiodipyridine.

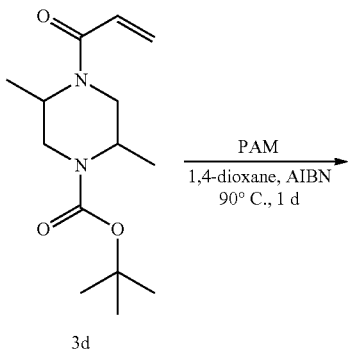

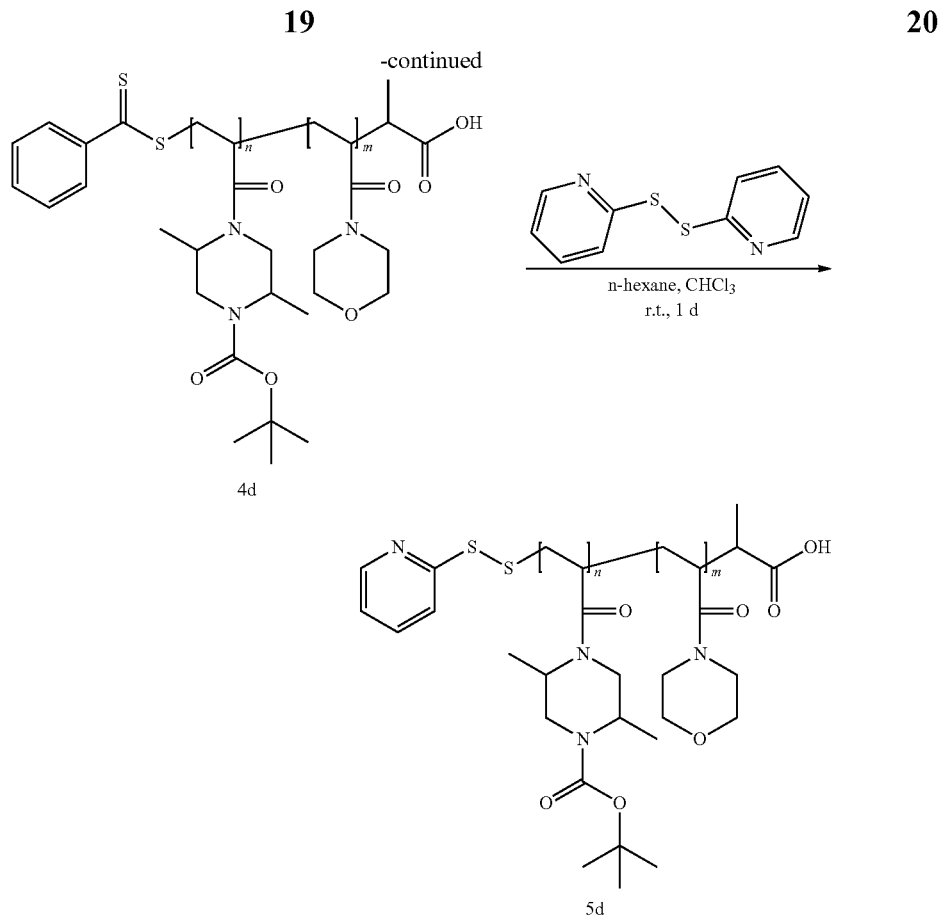

In order to synthesize poly[(N-acryloylmorpholine)-bl-(1-Boc-4-acryloyl-2,5-dimethylpiperazine)] (PAM-BocPAZd, 4d), PAM was synthesized as reported earlier[33] and introduced as a macromolecular chain transfer agent, hereafter termed macro CTA. As for PAM-BocPAZd, the degree of polymerization was determined as 146.2 (targeted: 200) by $^1$H NMR. 0.58 g ($2.78 \times 10^{-5}$ mol) of macro CTA was mixed with 0.38 g ($1.39 \times 10^{-3}$ mol) of 1-Boc-4-acryloyl-2,5-dimethylpiperazine (BocAZd) and 0.457 mg ($2.78 \times 10^{-6}$ mol) of AIBN in 3-4 mL of 1,4-dioxane in a Schlenk tube. Other conditions were identical to homopolymerization. In case of diblock terpolymer synthesis, the identical conditions were employed except for the monomer fed; the mixture of N-acryloylmorpholine (AM) and BocAZd were fed. The ratio between two monomers was 10:90 for $PAM_{142}$-bl-($PAM_{2.5}$-r-PAZd•$NONOate_{23}$).

3.4. End Group Modification by Aminolysis: BocPAZ-pyr (5a), BocPAZh-pyr (5b), BocPAZd-pyr (5c), PAM-Boc-PAZd-pyr (5d)

Respective homopolymers/copolymer (4a, 4b, 4c, 4d, 0.099 mmol) was first thoroughly mixed with 2,2'-dithiodipyridine (2.5 g, 11.3 mmol) in 139 mL $CHCl_3$ and n-hexylamine (1.15 g, 11.3 mmol) was added to. The reaction was preceded overnight. The clear yellow solution was extracted with equal volume of 1 M $KHSO_4$ (aq) (×2) and $H_2O$ and precipitated in cold n-hexane. Polymers (5a-5d) were recovered in 70-80% isolated yield.

3.5. Deprotection of Amine Groups

Respective polymer (5a-5d) (0.5 g) was dissolved in 100 mL of a 1:1 mixture of $CH_2Cl_2$/TFA and stirred overnight. The residue obtained, after removal of $CH_2Cl_2$ and TFA in a stream of Ar gas, was dissolved in methanol (5a, 5b) or NMP (5c, 5d), and precipitated in cold diethyl ether (×3). Polymers (6a-6d) were recovered in 70-85% isolated yield.

3.6. Basicification

Respective polymer (6a-6d) (0.6 g, 0.042 mmol) was dissolved in 10 mL of 0.5 M sodium methoxide-methanol solution (6a, 6b) or 5 mL of NMP mixed with 5 mL of 0.5 M sodium methoxide-methanol solution (6c, 6d). The basicified polymer solutions were dialyzed (MWCO: 3,500 Da) against water for 2 d and recovered by lyophilization. Polymers (7a-7d) were recovered in 20-80% isolated yield.

3.7. NONOation-I: Homopolymer

Respective polymer (7a-7c) (0.3 g) was dissolved in 10 mL of 0.5 M sodium methoxide-methanol solution, loaded into the high pressure reactor and purged with Ar for 1 h. The Ar flow was stopped and the high pressure reactor was filled with NO gas to a final pressure of 80 psi. In 1 d, pressure was increased to 120 psi and In 2 d, the pressure was increased up to 150 psi. In 5 d, the pressure was reduced to atmospheric pressure and the reactor was purged with Ar gas for 1 h to remove residual NO. The pale yellow solid was filtered and washed with methanol (8a, 8b) or directly precipitated in cold diethyl ether (8c). Polymers (8a-8c) were recovered in 60-80% isolated yield.

Scheme 4. Deprotection, basicification, and NONOation of homopolymers

Scheme 5. Deprotection, basicification, and NONOation of diblock copolymer

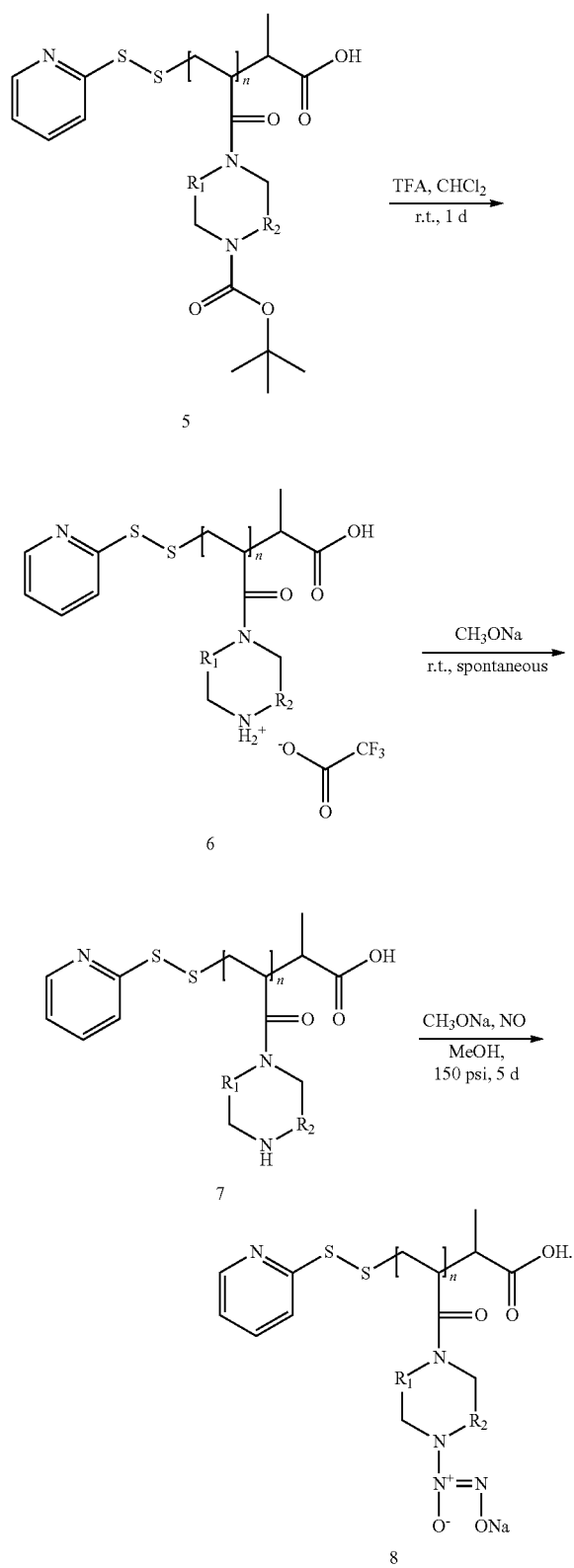
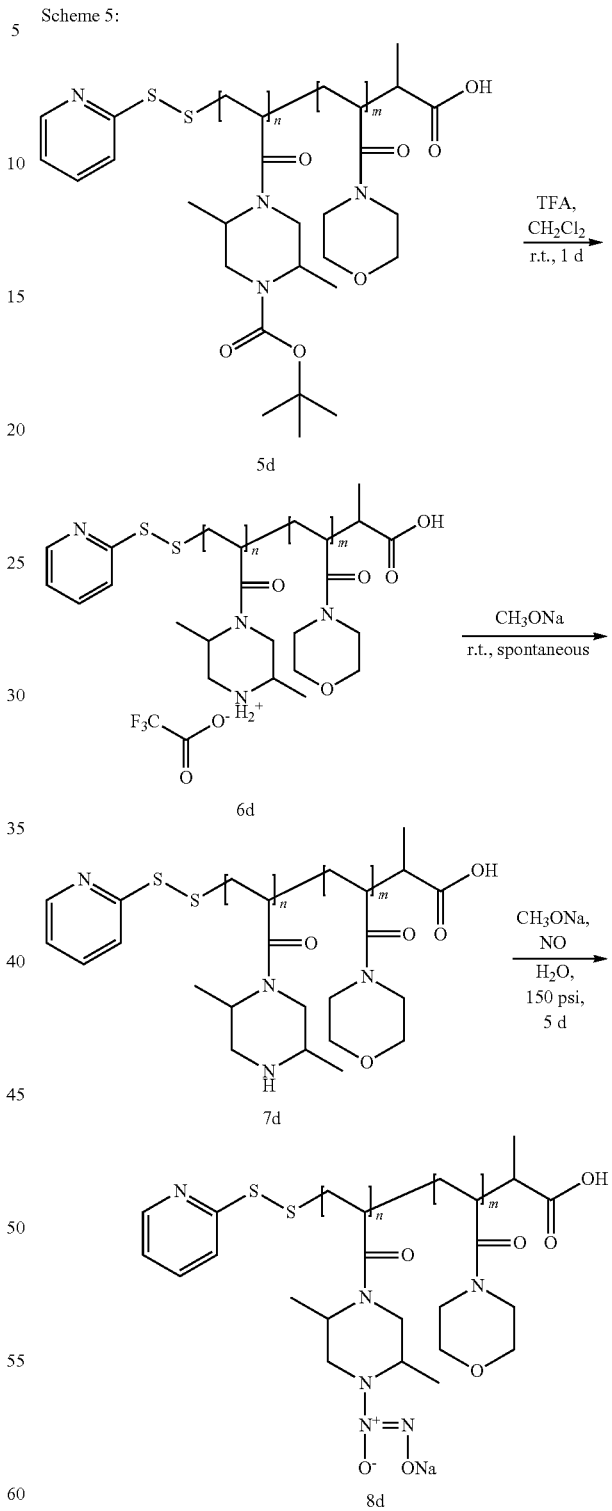

a: $R_1 = CH_2, R_2 = CH_2$
b: $R_1 = CH_2CH_2, R_2 = CH_2$
c: $R_1 = CH_3CH, R_2 = CH_3CH$ 3.8. NONOation-II and in Situ Micellazation of PAM-PAZd•NONOate (8d)

PAM-PAZd (7d) (0.1 g) was dissolved in 10 mL of MILLI-Q water. The amount of sodium methoxide added was varied with different conditions as described in the main manuscript. The aqueous solution was loaded into the high pressure reactor and purged with Ar for 2 h. The Ar flow was stopped and the high pressure reactor was filled with NO gas to a final pressure of 80 psi. In 1 d, the pressure was increased to 120 psi, which maintained for 3 d more. In 5 d, the pressure was reduced to atmospheric pressure and the reactor was purged with Ar gas for 2 h to remove residual NO. The solution was lyophilized and kept in Ar at −20° C. until subjected to characterization. (Average isolated yield: 95%)

4. NO Release Analysis

4.1. UV Absorbance Measurement

As for PAZ•NONOate and PAZh•NONOate, UV absorbance of polymer solution (0.05 mg/mL) was immediately scanned from 400 nm to 200 nm was scanned from 400 nm to 200 nm of wavelength at specific temperature (0° C. or 25° C. or 37° C.). Measurement was immediately carried out as soon as polymer solution was prepared in an adequate buffer. Data was unavailable for PAZd•NONOate due to poor solubility in water. The results are displayed in FIG. 13.

4.2. Free Radical Analyzer

NO analysis was performed with APOLLO 1000 free radical analyzer equipped with multi-port chamber, ISO-NOP NO sensor, and Lab-Trax-4/16. This experimental assembly was purchased from WPI instrument (Sarasota, USA). Temperature was maintained at 37° C. using water circulator. NO sensor was equilibrated in bi-distilled water for 1 d and 700 μL of PBS in multi-port chamber at 37° C. for overnight before the measurement started. As for PAZ•NONOate and PAZh•NONOate, 1-2 mg was weighed, dissolved in PBS (pH 7.4, 0.1 M), vortexed, and 300 μL was immediately drawn and injected into the chamber. As for PAZd•NONOate, 30 mg of weighed, suspended in 300 μL of PBS (pH 7.4, 0.1 M), and injected into chamber. As for PAM-PAZd•NONOate, 30 mg of lyophilized solid was weighed, re-dispersed in 300 μL PBS (pH 7.4, 0.1 M), vortexed, and injected into chamber. As for terpolymer, 10 mg of lyophilized solid was weighed, re-dispersed in 300 μL PBS (pH 7.4, 0.1 M), vortexed, and injected into chamber. Data was acquired with Data-Trax software (WPI instrument, Sarasota, USA) with a sampling rate of 1 sec/sample.

5. Nanoparticle Infusion in Rabbit Carotid Artery Ex Vivo

5.1. Labelling of Nanoparticles (Scheme 6)

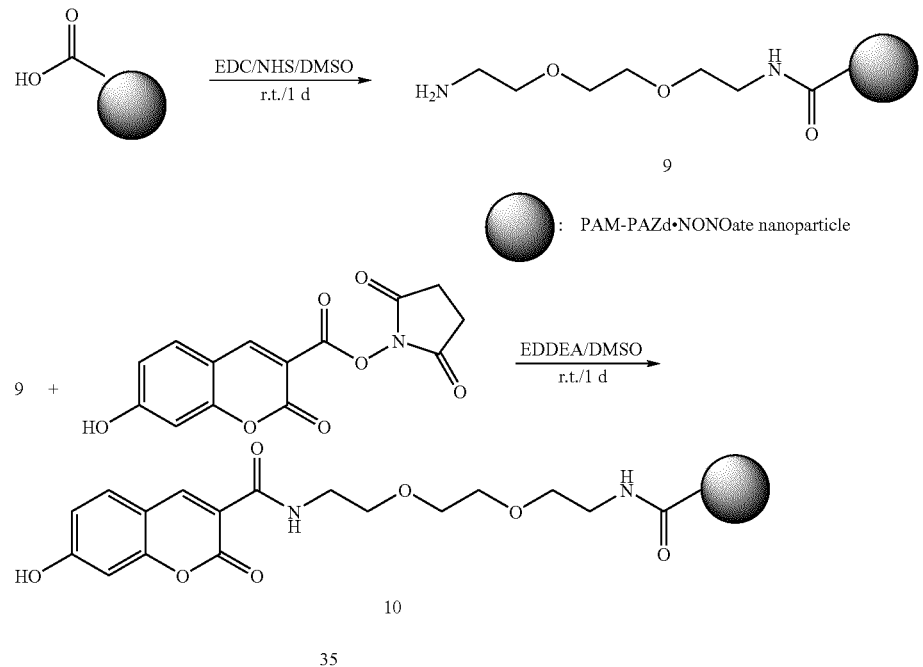

Figure 14:
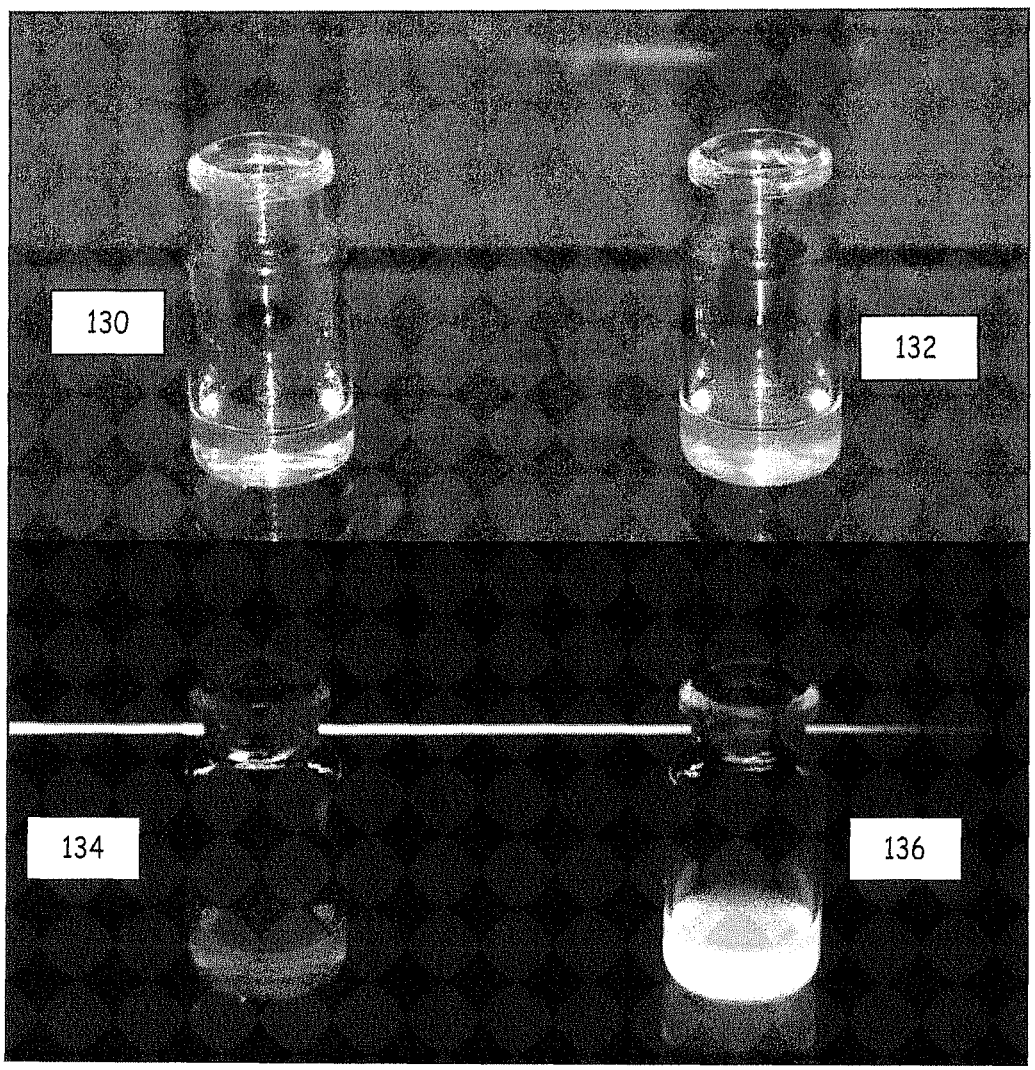
FIG. 14 are images of $PAM_{146}$-$PAZdNONOate_{23}$ micelles (130, 132, 134, 136) that are coumarin-labeled (132, 136) or not so labeled (130, 134) as visualized under visible light (130, 132) or ultraviolet light (134, 136)

Scheme 6. Fluorescent labeling of PAM-PAZd•NONOate nanoparticles $PAM_{146}$-PAZd•NONOate$_{23}$ micelles (0.1 g, $0.4\times10^{-5}$ mol of carboxylic acid groups on the particles) was mixed with 50-fold excess of EDDEA (0.03 g, $2.0\times10^{-4}$ mol), EDC (0.038 g, $2.0\times10^{-4}$ mol), and sulfo-NHS (0.043 g, $2.0\times10^{-4}$ mol) in 1 mL of distilled water to obtain the activated micelles (9, average diameter: 59±0.7 nm). Then, removing unreacted reagents by dialysis overnight, 50-fold excess of coumarin-NHS solution dissolved in 100 μL of acetone was added to the aforementioned micellar suspension. Reacting overnight with stirring, unreacted coumarin-NHS was removed by centrifugation (13,000 rpm, 10 min) and supernatant containing coumarin-labelled micelles (10, average diameter: 62±0.6 nm) was dialyzed for 2 d under darkness. Visualized images are shown in FIG. 14.

5.2. Ex Vivo Infusion of Nanoparticles in Rabbit Carotid Artery

Fixed arteries were sectioned into slices and observed with Zeiss AXIOVERT 200M fluorescence microscope (Jena, Germany). See methods above.

6. Homopolymer Characterization

6.1. poly(N-acryloylpiperazine) Series (BocPAZ, PAZ-TFA, PAZ, PAZ•NONOate)

Poly(1-Boc-4-acryloylpiperazine) (BocPAZ, 4a) $^1$H NMR (400 MHz, CDCl$_3$) δ 8.04-7.83 (m, ArH, end group), 7.64-7.51 (m, ArH, end group), 7.50-7.35 (m, ArH, end group), 5.26-5.01 (m, CH, end group), 4.49-2.93 (m, CH$_2$, piperazine ring), 2.93-2.14 (m, CH, acrylamide chain), 2.14-0.50 (m, CH$_2$, acrylamide chain, C(CH$_3$)$_3$, Boc group), 1.46 (s, C(CH$_3$)$_3$, Boc group); $^{13}$C{$^1$H} CPMAS NMR (75 MHz) δ 173.5 (N—C=O), 154.2 (N—COO—), 79.4 (C—(CH$_3$)$_3$), 44.0 (CH$_2$—N), 36.1 (CH$_2$—CH), 28.8 (CH$_3$); FT-IR:

2976.20, 1697.90, 1640.28, 1455.59, 1415.59, 1365.56, 1284.55, 1250.40, 1233.72, 1165.74, 1124.28, 1077.70, 1022.17, 995.90, 863.04, 770.47 cm$^{-1}$; $\overline{M}_n$ ($^1$H NMR)=13510 (degree of polymerization: 55.3); $\overline{M}_w/\overline{M}_n$ (SEC)=1.04.

Assignation for dithiopyridinyl end groups: BocPAZ-pyr (5a) $^1$H NMR (400 MHz, CDCl$_3$) δ 8.54-8.34 (m, 1H), 7.73-7.56 (m, 2H), 7.20-7.03 (m, 1H).

Poly(N-acryloylpiperazine)trifluoroacetate salt (PAZ•TFA) (6a) $^1$H NMR (400 MHz, DMSO-d$_6$) δ 10.62-8.56 (broad s, NH$_2^+$, protonated secondary amine on piperazine ring), 8.56-8.34 (m, ArH, end group), 7.90-7.73 (m, ArH, end group), 7.73-7.46 (m, ArH, end group), 7.39-7.18 (m, ArH, end group), 4.79-2.76 (m, CH$_2$, piperazine ring), 2.76-2.10 (m, CH$_2$, piperazine ring), 2.76-2.10 (CH, acrylamide chain), 2.10-0.60 (CH$_2$, acrylamide chain); $^{13}$C{$^1$H} CPMAS NMR (75 MHz) δ 173.4 (N—C=O), 162.4 (COO$^-$), 117.0 (CF$_3$), 43.3 (CH$_2$—N), 38.0 (CH$_2$—N), 35.0 (CH$_2$—CH); FT-IR: 2742.11, 1672.43, 1644.90, 1440.64, 1250.23, 1198.50, 1126.56, 1024.73, 940.38, 834.22, 798.19, 721.44 cm$^{-1}$.

Poly(N-acryloylpiperazine) (PAZ) (7a) $^1$H NMR (400 MHz, 0.1 M NaOD in D$_2$O) δ 3.62-2.71 (bs, CH$_2$, piperazine ring), 2.66-2.10 (bs, CH, acrylamide chain), 1.66-0.65 (m, CH$_2$, acrylamide chain); $^{13}$C NMR: 173.4 (s, N—C=O), 46.9 (s, CH$_2$—N), 44.4 (s, CH$_2$—N), 36.4 (s, CH$_2$—CH); FT-IR: 2914.61, 1622.26, 1436.78, 1361.65, 1231.34, 1139.34, 1025.84, 811.98 cm$^{-1}$.

Poly(sodium 1-(N-acryloylpiperazin-1-yl)diazen-1-ium-1,2-diolate) (PAZ•NONOate) (8a) $^1$H NMR (400 MHz, 0.1 M NaOD in D$_2$O) δ3.91-3.22 (bs, CH$_2$, piperazine ring), 3.19-2.72 (bs, CH$_2$, piperazine ring), 2.70-2.21 (bs, CH, acrylamide chain), 1.86-0.71 (m, CH$_2$, acrylamide chain); $^{13}$C{$^1$H} CPMAS NMR (75 MHz) δ 174.3 (N—C=O), 52.7 (CH$_2$—N), 44.8-41.3(CH$_2$—N), 36.6 (CH$_2$—CH); FT-IR: 3375.12, 1619.21, 1444.46, 1358.69, 1227.65, 1175.91, 1031.59, 952.12 cm$^{-1}$.

6.2. poly(N-acryloylhomopiperazine) Series (BocPAZh, PAZh•TFA, PAZh, PAZh•NONOate)

Poly(1-Boc-4-acryloylhomopiperazine) (BocPAZh, 4b) $^1$H NMR (400 MHz, CDCl$_3$) δ 8.07-7.83 (m, ArH, end group), 7.64-7.48 (m, ArH, end group), 7.47-7.33 (m, ArH, end group), 5.28-4.90 (m, CH, end group), 4.30-2.87 (m, CH$_2$, homopiperazine ring), 2.87-2.21 (m, CH, acrylamide chain), 2.18-0.94 (m, CH$_2$, acrylamide chain, C(CH$_3$)$_3$, Boc group, CH$_2$, homopiperazine ring), 1.45 (s, C(CH$_3$)$_3$, Boc group); $^{13}$C{$^1$H} CPMAS NMR (75 MHz) δ 173.6 (N—C=O), 154.6 (N—COO—), 78.8 (C—(CH$_3$)$_3$), 46.3 (CH—N, CH$_2$—CH$_2$—CH$_2$), 35.6 (CH$_2$—CH), 28.3 ((CH$_3$)$_3$—C); FT-IR: 2974.43, 1692.74, 1636.41, 1415.41, 1365.57, 1304.34, 1241.46, 1164.14, 1126.55, 1079.33, 993.17, 927.47, 858.84, 771.88 cm$^{-1}$; $\overline{M}_n$ ($^1$H NMR)=15180 (degree of polymerization: 58.8); $\overline{M}_w/\overline{M}_n$ (SEC)=1.04.

Assignation for dithiopyridinyl end groups: BocPAZh-pyr (5b) $^1$H NMR (400 MHz, CDCl$_3$) δ 8.51-8.32 (m, 1H), 7.70-7.58 (m, 2H), 7.17-7.04 (m, 1H).

Poly(N-acryloylhomopiperazine)trifluoroacetate salt (PAZh•TFA) (6b); $^1$H NMR (400 MHz, DMSO-d$_6$) δ 10.50-8.57 (broad s, NH$_2^+$, protonated secondary amine on homopiperazine ring), 8.53-8.34 (m, ArH, end group), 7.87-7.73 (m, ArH, end group), 7.73-7.53 (m, ArH, end group), 7.41-7.00 (m, ArH, end group), 5.08-2.84 (m, CH$_2$, homopiperazine ring), 2.84-2.29 (CH, acrylamide chain), 2.29-0.52 (CH$_2$, acrylamide chain, CH$_2$, homopiperazine ring); $^{13}$C{$^1$H} CPMAS NMR (75 MHz) δ 172.8 (N—C=O), 159.5 (COO$^-$), 114.9 (CF$_3$), 42.7 (CH$_2$—N), 32.6 (CH$_2$—CH), 23.2 (CH$_2$—CH$_2$—CH$_2$); FT-IR=2853.75, 1673.83, 1633.78, 1429.01, 1371.39, 1197.96, 1125.35, 833.64, 798.39, 720.95 cm$^{-1}$. Poly(N-acryloylhomopiperazine) (PAZh) (7b); $^{-1}$H NMR (400 MHz, 0.1M NaOD in D$_2$O) δ 4.03-3.13 (m, CH$_2$, homopiperazine ring), 3.13-2.26 (m, CH$_2$, homopiperazine ring, CH, acrylamide chain) 2.26-0.77 (CH$_2$, homopiperazine ring, CH$_2$, acrylamide chain); $^{13}$C{$^1$H} CPMAS NMR (75 MHz) δ 172.0 (N—C=O), 45.7 (CH$_2$—N), 33.7 (CH$_2$—CH), 24.0 (CH$_2$—CH$_2$—CH$_2$); FT-IR=3303.91, 2929.63, 1617.77, 1447.85, 1365.89, 1288.86, 1206.37, 1143.79, 952.61, 767.60 cm$^{-1}$.

Poly(sodium 1-(N-acryloylhomopiperazin-1-yl)diazen-1-ium-1,2-diolate) (PAZh•NONOate) (8b); $^1$H NMR (400 MHz, 0.1M NaOD in D$_2$O) δ 4.19-3.03 (m, CH$_2$, homopiperazine ring), 3.03-2.32 (m, CH, acrylamide chain) 2.32-0.59 (CH$_2$, homopiperazine ring, CH$_2$, acrylamide chain); $^{13}$C{$^1$H} CPMAS NMR (75 MHz) δ 174.4 (N—C=O), 52.4 (CH—N), 44.3 (CH$_2$—N), 33.9 (CH$_2$—CH), 24.6 (CH$_2$—CH$_2$—CH$_2$); FT-IR=2931.60, 1623.74, 1433.54, 1353.82, 1222.49, 935.10, 787.87 cm$^{-1}$.

6.3. poly(N-acryloyl-2,5-dimethylpiperazine) Series (BocPAZd, PAZd•TFA, PAZd, PAZd•NONOate)

Poly(1-Boc-4-acryloyl-2,5-dimethylpiperazine) (BocPAZd, 4c) $^1$H NMR (400 MHz, CDCl$_3$) δ 8.10-7.75 (m, ArH, end group), 7.68-7.47 (m, ArH, end group), 7.47-7.31 (m, ArH, end group), 5.00-2.52 (m, CH$_2$, CH, 2,5-dimethylpiperazine ring), 2.52-1.62 (m, CH, acrylamide chain), 1.36-0.35 (m, CH$_2$, acrylamide chain, CH$_3$, methyl group on the 2,5-dimethylpiperazine ring), 1.45 (s, C(CH$_3$)$_3$, Boc group); $^{13}$C{$^1$H} CPMAS NMR (75 MHz) δ 173.2 (N—C=O), 154.2 (N—COO—), 78.8 (C—(CH$_3$)$_3$), 47.1 (CH—N), 44.2 (CH$_2$—N), 36.0 (CH$_2$—CH), 28.3 ((CH$_3$)$_3$—C), 15.1 (CH$_3$—CH); FT-IR: 2973.84, 2932.91, 2872.29, 2300.20, 1694.25, 1635.23, 1416.15, 1365.00, 1331.04, 1312.31, 1272.09, 1168.64, 1130.10, 1102.97, 1063.52, 1051.73, 867.62, 815.41, 766.58 cm$^{-1}$; $\overline{M}_n$ ($^1$H NMR)=16540 (degree of polymerization: 60.8); $\overline{M}_w/\overline{M}_n$ (SEC)=1.09.

Assignation for dithiopyridinyl end groups: BocPAZd-pyr (5c) $^1$H NMR (400 MHz, CDCl$_3$) δ 8.54-8.26 (m, 1H), 7.75-7.38 (m, 2H), 7.17-6.89 (m, 1H).

Poly(N-acryloyl-2,5-dimethylpiperazine)trifluoroacetate salt (PAZd•TFA) (6c) $^1$H NMR (400 MHz, DMSO-d$_6$) δ 10.20-8.74 (broad s, NH$_2^+$, protonated secondary amine on 2,5-dimethylpiperazine ring), 8.56-8.37 (m, ArH, end group), 7.91-7.71 (m, ArH, end group), 7.71-7.46 (m, ArH, end group), 7.36-7.17 (m, ArH, end group), 5.15-2.79 (m, CH, CH$_2$, 2,5-dimethylpiperazine ring), 2.79-2.05 (CH, acrylamide chain), 2.05-0.50 (CH$_2$, acrylamide chain, CH$_3$, 2,5-dimethylpiperazine ring); $^{13}$C{$^1$H} CPMAS NMR (75 MHz) δ 173.5 (N—C=O), 161.7 (CF$_3$COO—), 117.2 (CF$_3$COO—), 47.2 (CH—N), 41.6 (CH$_2$—N), 36.1 (CH$_2$—CH), 14.1 (CH$_3$—CH); FT-IR: 2983.55, 1669.92, 1634.40, 1428.49, 1353.70, 1244.79, 1197.42, 1127.39, 1066.24, 1034.46, 834.36, 798.18, 720.63 cm$^{-1}$.

Poly(N-acryloyl-2,5-dimethylpiperazine) (PAZd) (7c) $^1$H NMR (400 MHz, 0.1M NaOD in D$_2$O) δ 4.64-2.03 (m, CH$_2$, CH, 2,5-dimethylpiperazine ring, CH, acrylamide chain), 1.99-0.18 (CH$_3$, methyl group on 2,5-dimethylpiperazine ring, CH$_2$, acrylamide chain); $^{13}$C{$^1$H} CPMAS NMR (75 MHz) δ 173.9 (N—C=O), 46.5 (CH—N), 44.3 (CH$_2$—N), 36.1 (CH$_2$—CH), 15.9 (CH$_3$—CH); FT-IR: 3293.32, 2967.41, 1621.95, 1435.22, 1373.82, 1244.05, 1159.58, 1066.77, 791.59 cm$^{-1}$.

Poly(sodium 1-(N-acryloyl-2,5-dimethylpiperazin-1-yl)diazen-1-ium-1,2-diolate) (PAZd•NONOate) (8c) Solution state $^1$H NMR spectra are unavailable due to the limited solubility in most of solvents available; $^{13}$C{$^1$H} CPMAS NMR (75 MHz) δ 174.4 (N—C=O), 54.5, 51.4 (CH—N), 49.6, 44.9 (CH$_2$—N), 37.8 (CH$_2$—CH), 16.1 (CH$_3$—CH);

FT-IR: 2975.76, 1638.69, 1427.19, 1361.73, 1308.58, 1263.90, 1165.02, 1099.28, 1064.48, 1033.61, 935.27, 771.38 cm$^{-1}$.

7. Block Copolymer Characterization

Poly[(N-acryloylmorpholine)-bl-(1-Boc-4-acryloyl-2,5-dimethylpiperazine)] (PAM-BocPAZd, 4d) Isolated yield: 68%; $^1$H NMR (400 MHz, CDCl$_3$) δ 8.07-7.75 (m, ArH, end group), 7.75-7.46 (m, ArH, end group), 7.46-7.33 (m, ArH, end group), 4.94-2.82 (m, CH, CH$_2$, morpholine ring and 2,5-dimethylpiperazine ring), 2.80-2.15 (m, CH, acrylamide chain), 2.14-0.45 (m, CH$_2$, acrylamide chain, CH$_3$, methyl group on 2,5-dimethylpiperazine ring, C(CH$_3$)$_3$, Boc group), 1.46 (s, C(CH$_3$)$_3$, Boc group); $^{13}$C{$^1$H} CPMAS NMR (75 MHz) δ 173.6 (N—C=O), 154.6 (N—COO—), 79.0 (C—(CH$_3$)$_3$), 66.8 (CH$_2$—O), 45.8 (CH$_2$—N), 42.4 (CH$_2$—N), 35.6 (CH$_2$—CH), 28.0 ((CH$_3$)$_3$—C), 15.0 (CH—CH$_3$); FT-IR: 3490.95, 2971.66, 1697.47, 1633.86, 1439.99, 1365.52, 1310.38, 1268.88, 1237.16, 1172.16, 1113.17, 1066.42, 1030.74, 846.15, 767.27 cm$^{-1}$; $\overline{M}_n$ ($^1$H NMR, PAM)=20870; $\overline{M}_w/\overline{M}_n$ (SEC, PAM)=1.03; $\overline{M}_n$ ($^1$H NMR, PAM$_{146}$-Boc-PAZd$_{57}$)=30940, $\overline{M}_n$ ($^1$H NMR, PAM$_{146}$-Boc-PAZd$_{23}$)=27440; $\overline{M}_w/\overline{M}_n$ (SEC, PAM$_{146}$-Boc-PAZd$_{57}$)=1.06.

Assignation for dithiopyridinyl end groups: PAM-Boc-PAZd-pyr (5d) $^1$H NMR (400 MHz, CDCl$_3$) δ 8.51-8.39 (m, 1H), 7.68-7.57 (m, 2H), 7.16-7.07 (m, 1H).

Poly[(N-acryloylmorpholine)-bl-(N-acryloyl-2,5-dimethylpiperazine)]trifluoroacetate salt (PAM-PAZd•TFA) (6d) $^1$H NMR (400 MHz, DMSO-d$_6$) δ 10.49-8.62 (broad s, NH$_2^+$, protonated secondary amine on 2,5-dimethylpiperazine ring), 8.55-8.31 (m, ArH, end group), 7.94-7.73 (m, ArH, end group), 7.73-7.51 (m, ArH, end group), 7.42-7.12 (m, ArH, end group), 5.23-2.79 (m, CH$_2$, morpholine ring, CH, CH$_2$, 2,5-dimethylpiperazine ring), 2.79-2.06 (m, CH, acrylamide chain), 1.97-0.53 (CH$_2$, acrylamide chain, CH$_3$, methyl group on 2,5-dimethylpiperazine ring); $^{13}$C{$^1$H} CPMAS NMR δ 173.4 (N—C=O), 161.5 (COO$^-$), 117.2 (CF$_3$), 66.8 (CH$_2$—O), 45.8 (CH—CH$_3$), 42.4 (CH$_2$—N), 35.6 (CH$_2$—CH), 15.0 (CH—CH$_3$); FT-IR: 3472.88, 2858.17, 1630.81, 1438.34, 1359.72, 1302.08, 1268.18, 1200.69, 1113.05, 1067.70, 1030.67, 838.71, 799.55, 721.62 cm$^{-1}$.

Poly[(N-acryloylmorpholine)-bl-(N-acryloyl-2,5-dimethylpiperazine)] (PAM-PAZd) (7d) $^1$H NMR (400 MHz, 0.1 M NaOD in D$_2$O) δ 4.57-2.90 (m, CH$_2$, morpholine ring and 2,5-dimethylpiperazine ring), 2.90-2.19 (CH, acrylamide chain), 2.19-0.56 (CH$_2$, acrylamide chain, CH$_3$, methyl group); $^{13}$C{$^1$H} CPMAS NMR (75 MHz) δ 171.5 (N—C=O), 64.4 (CH$_2$—O), 48.0 (CH$_2$—N, CH—N), 43.8 (CH$_2$—N, CH—N), 40.1 (CH$_2$—N), 33.4 (CH$_2$—CH), 13.6 (CH—CH$_3$); FT-IR: 2856.52, 1631.37, 1435.68, 1360.70, 1300.46, 1267.56, 1232.48, 1112.48, 1067.59, 1029.67, 844.89 cm$^{-1}$.

Poly[(N-acryloylmorpholine)-bl-(sodium 1-(N-acryloyl-2,5-dimethylpiperazin-1-yl)diazen-1-ium-1,2-diolate)] (PAM-PAZd•NONOate) (8d) $^{13}$C {$^1$H} CPMAS NMR (75 MHz) δ 172.0 (N—C=O), 64.1 (CH$_2$—O), 51.6 (CH$_2$—N, CH—N), 43.8 (CH$_2$—N, CH—N), 40.9 (CH$_2$—N), 33.4 (CH$_2$—CH), 13.4 (CH—CH$_3$); FT-IR: 2862.18, 1631.36, 1434.66, 1360.27, 1266.63, 1111.34, 1065.57, 1030.23, 936.63, 836.07 cm$^{-1}$.

Various embodiments have been described herein by way of example with certain features. In general, these features may be mixed-and-matched to make additional embodiments as guided by the need to make embodiments of the invention that are functional.

TABLE 1

Properties of polymers.

| Table Item no. | Structure | Abbreviation of polymer | Type of polymer | $t_{1/2}$ | Solubility in water | Mean diameter (nm) |
|---|---|---|---|---|---|---|
| 1 | [structure, n = 55] | PAZ · NONOate | Homopolymer | 17 mins | Yes | — |
| 2 | [structure, n = 59] | PAZh · NONOate | Homopolymer | 24 mins | Yes | — |
| 3 | [structure, n = 61] | PAZd · NONOate | Homopolymer | N/A | No | — |

TABLE 1-continued

Properties of polymers.

| Table Item no. | Structure | Abbreviation of polymer | Type of polymer | $t_{1/2}$ | Solubility in water | Mean diameter (nm) |
|---|---|---|---|---|---|---|
| 4 | 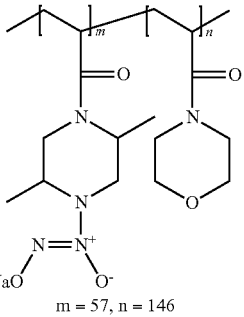<br>m = 57, n = 146 | PAM$_{146}$-PAZd · NONOate$_{57}$ | Diblock copolymer | 21 d | Aggregates | 110 |
| 5 | 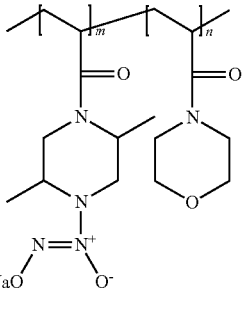<br>m = 23, n = 146 | PAM$_{146}$-PAZd · NONOate$_{23}$-1 | Diblock copolymer | 20 d | Aggregates | 79 |
| 6 | 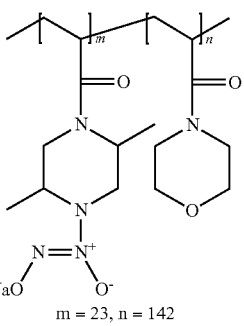<br>m = 23, n = 142 | PAM$_{142}$-PAZd · NONOate$_{23}$-2 | Diblock copolymer | 6.5 d | Aggregates | 52 |
| 7 | 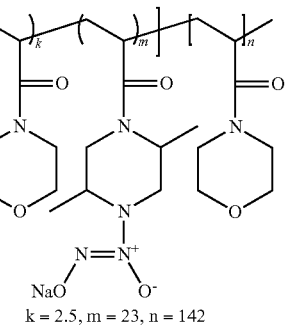<br>k = 2.5, m = 23, n = 142 | PAM$_{142}$-(PAM$_{2.5}$-r-PAZd · NONOate$_{23}$) | Diblock terpolymer | 1.9 d | Unimer or unstable aggregates | — |

TABLE 1-continued

Properties of polymers.

| Table Item no. | Structure | Abbreviation of polymer | Type of polymer | $t_{1/2}$ | Solubility in water | Mean diameter (nm) |
|---|---|---|---|---|---|---|
| 8 | 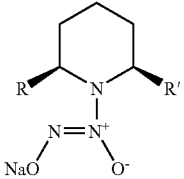 A: R = R' = H, B: R = H, R' = CH$_3$, C: R = R' = CH$_3$ | From ref. 1 | — | A: 78 s, B: 8.3 mins, C: 50 mins | Monomeric molecule | — |

TABLE 2A)

Solubility of poly(N-acryloylpiperazine) series (BocPAZ, PAZ•TFA, PAZ, PAZ•NONOate)

| Table Item No. | | Polarity index[3] | BocPAZ | PAZ•TFA | PAZ | PAZ•NONOate |
|---|---|---|---|---|---|---|
| 1 | Water | 9.0 | Insoluble | Soluble | Soluble | Soluble |
| 2 | Formamide | 7.3 | Swollen | Soluble | Soluble | Insoluble |
| 3 | Nitromethane | 6.8 | Soluble | Insoluble | Insoluble | Insoluble |
| 4 | Methanol | 6.6 | Soluble | Soluble | Soluble | Insoluble |
| 5 | DMSO | 6.5 | Soluble | Soluble | Swollen | Insoluble |
| 6 | NMP | 6.5 | Soluble | Soluble | Insoluble | Insoluble |
| 7 | DMF | 6.4 | Soluble | Soluble | Insoluble | Insoluble |
| 8 | DMAc | 6.3 | Soluble | Soluble | Insoluble | Insoluble |
| 9 | Acetonitrile | 6.2 | Soluble | Insoluble | Insoluble | Insoluble |
| 10 | Acetone | 5.4 | Soluble | Insoluble | Insoluble | Insoluble |
| 11 | Ethanol | 5.2 | Soluble | Insoluble | Insoluble | Insoluble |
| 12 | 1,4-dioxane | 4.8 | Soluble | Insoluble | Insoluble | Insoluble |
| 13 | Chloroform | 4.4 | Soluble | Insoluble | Insoluble | Insoluble |
| 14 | Iso-propanol | 4.3 | Soluble | Insoluble | Insoluble | Insoluble |
| 15 | Ethyl acetate | 4.3 | Soluble | Insoluble | Insoluble | Insoluble |
| 16 | THF | 4.2 | Soluble | Insoluble | Insoluble | Insoluble |
| 17 | DCM | 3.4 | Soluble | Insoluble | Insoluble | Insoluble |
| 18 | Toluene | 2.3 | Soluble | Insoluble | Insoluble | Insoluble |
| 19 | n-hexane | 0.0 | Insoluble | Insoluble | Insoluble | Insoluble |

TABLE 2b

Solubility of poly(N-acryloylhomopiperazine) series (BocPAZh, PAZh•TFA, PAZh, PAZh•NONOate)

| Table Item No. | | Polarity index[3] | BocPAZh | PAZh•TFA | PAZh | PAZh•NONOate |
|---|---|---|---|---|---|---|
| 1 | Water | 9.0 | Insoluble | Soluble | Soluble | Soluble |
| 2 | Formamide | 7.3 | Insoluble | Soluble | Soluble | Insoluble |
| 3 | Nitromethane | 6.8 | Soluble | Insoluble | Insoluble | Insoluble |
| 4 | Methanol | 6.6 | Soluble | Soluble | Soluble | Insoluble |
| 5 | Dimethylsulfoxide (DMSO) | 6.5 | Soluble | Soluble | Insoluble | Insoluble |
| 6 | NMP (N-Methyl Pyrrolidone) | 6.5 | Soluble | Soluble | Insoluble | Insoluble |
| 7 | Dimethylformamide (DMF) | 6.4 | Soluble | Soluble | Insoluble | Insoluble |
| 8 | Dimethyl acetamide (DMAc) | 6.3 | Soluble | Soluble | Insoluble | Insoluble |
| 9 | Acetonitrile | 6.2 | Soluble | Insoluble | Insoluble | Insoluble |
| 10 | Acetone | 5.4 | Soluble | Insoluble | Insoluble | Insoluble |
| 11 | Ethanol | 5.2 | Soluble | Soluble | Soluble | Insoluble |
| 12 | 1,4-dioxane | 4.8 | Soluble | Insoluble | Insoluble | Insoluble |
| 13 | Chloroform | 4.4 | Soluble | Insoluble | Soluble | Insoluble |
| 14 | Iso-propanol | 4.3 | Soluble | Insoluble | Insoluble | Insoluble |
| 15 | Ethyl acetate | 4.3 | Soluble | Insoluble | Insoluble | Insoluble |

TABLE 2b-continued

Solubility of poly(N-acryloylhomopiperazine) series (BocPAZh, PAZh•TFA, PAZh, PAZh•NONOate)

| Table Item No. | | Polarity index[3] | BocPAZh | PAZh•TFA | PAZh | PAZh•NONOate |
|---|---|---|---|---|---|---|
| 16 | Terahydrofuran (THF) | 4.2 | Soluble | Insoluble | Insoluble | Insoluble |
| 17 | Dichloromthane (DCM) | 3.4 | Soluble | Insoluble | Insoluble | Insoluble |
| 18 | Toluene | 2.3 | Soluble | Swollen | Swollen | Insoluble |
| 19 | n-hexane | 0.0 | Insoluble | Insoluble | Insoluble | Insoluble |

TABLE 2c

Solubility of poly(N-acryloyl-2,5-dimethylpiperazine) series (BocPAZd, PAZd•TFA, PAZd, PAZd•NONOate)

| | Polarity index[3] | BocPAZd | PAZd•TFA | PAZd | PAZd•NONOate |
|---|---|---|---|---|---|
| Water | 9.0 | Insoluble | Soluble | Soluble | Insoluble |
| Formamide | 7.3 | Insoluble | Soluble | Soluble | Insoluble |
| Nitromethane | 6.8 | Soluble | Insoluble | Insoluble | Insoluble |
| Methanol | 6.6 | Soluble | Soluble | Soluble | Insoluble |
| DMSO | 6.5 | Swollen | Soluble | Soluble | Insoluble |
| NMP | 6.5 | Soluble | Soluble | Soluble | Insoluble |
| DMF | 6.4 | Soluble | Soluble | Soluble | Insoluble |
| DMAc | 6.3 | Soluble | Soluble | Soluble | Insoluble |
| Acetonitrile | 6.2 | Soluble | Insoluble | Insoluble | Insoluble |
| Acetone | 5.4 | Soluble | Insoluble | Insoluble | Insoluble |
| Ethanol | 5.2 | Soluble | Soluble | Soluble | Insoluble |
| 1,4-dioxane | 4.8 | Soluble | Insoluble | Insoluble | Insoluble |
| Chloroform | 4.4 | Soluble | Insoluble | Soluble | Insoluble |
| Iso-propanol | 4.3 | Soluble | Insoluble | Soluble | Insoluble |
| Ethyl acetate | 4.3 | Soluble | Insoluble | Insoluble | Insoluble |
| THF | 4.2 | Soluble | Insoluble | Insoluble | Insoluble |
| DCM | 3.4 | Soluble | Insoluble | Insoluble | Insoluble |
| Toluene | 2.3 | Soluble | Insoluble | Soluble | Insoluble |
| n-hexane | 0.0 | Insoluble | Insoluble | Insoluble | Insoluble |

REFERENCES

These references are hereby incorporated by reference herein; the specification of this application controls in case of conflict.

1. Moncada, S. & Higgs, E. A. The discovery of nitric oxide and its role in vascular biology. *Br. J Pharmacol.* 147, S193-S201 (2006).
2. Lamas, S., Perez-Sala, D. & Moncada, S. Nitric oxide: From discovery to the clinic. *Trends Pharmacol. Sci.* 19, 436-438 (1998).
3. Rothrock, A. R., Donkers, R. L. & Schoenfisch, M. H. Synthesis of nitric oxide-releasing gold nanoparticles. *J. Am. Chem. Soc.* 127, 9362-9363 (2005).
4. Zhang, H. P. et al. Nitric oxide-releasing fumed silica particles: Synthesis, characterization, and biomedical application. *J. Am. Chem. Soc.* 125, 5015-5024 (2003).
5. Zhou, Z., Annich, G. M., Wu, Y. & Meyerhoff, M. E. Water-soluble poly(ethylenimine)-based nitric oxide donors: Preparation, characterization, and potential application in hemodialysis. *Biomacromolecules* (2006).
6. Parzuchowski, P. G., Frost, M. C. & Meyerhoff, M. E. Synthesis and characterization of polymethacrylate-based nitric oxide donors. *J. Am. Chem. Soc.* 124, 12182-12191 (2002).
7. Popowich, D. A., varu, V. & Kibbe, M. R. Nitric oxide: What a vascular surgeon needs to know. *Vascular* 15, 324-335 (2007).
8. Ross, R. Atherosclerosis—an inflammatory disease. N. Engl. J. Med. 340, 115-126 (1999).
9. Weintraub, W. S. The pathophysiology and burden of restenosis. *Am. J. Cardiol.* 100, S3-S9 (2007).
10. Schainfeld, R. M. Potential emerging therapeutic strategies to prevent restenosis in the peripheral vasculature. *Catheter. Cardiovasc. Interv.* 56, 421-431 (2002).
11. Ettenson, D. S. & Edelman, E. R. Local drug delivery: An emerging approach in the treatment of restenosis. *Vasc. Med.* 5, 97-102 (2000).
12. Acharya, G. & Park, K. Mechanisms of controlled drug release from drug-eluting stents. *Adv. Drug Delivery Rev.* 58, 387-401 (2006).
13. Dzau, V. J., Braun-Dullaeus, R. C. & Sedding, D. G. Vascular proliferation and atherosclerosis: New perspectives and therapeutic strategies. *Nat. Med.* 8, 1249-1256 (2002).
14. Herman, A. G. & Moncada, S. Therapeutic potential of nitric oxide donors in the prevention and treatment of atherosclerosis. *Eur. Heart J.* 26, 1945-1955 (2005).
15. Babapulle, M. N. & Eisenberg, M. J. Coated scents for the prevention of restenosis: Part ii. *Circulation* 106, 2859-2866 (2002).
16. Babapulle, M. N. & Eisenberg, M. J. Coated stents for the prevention of restenosis: Part i. *Circulation* 106, 2734-2740 (2002).
17. Lancaster, J. R. A tutorial on the diffusibility and reactivity of free nitric oxide. *Nitric Oxide-Biol. Chem.* 1, 18-30 (1997).

18. Vaughn, M. W., Kuo, L. & Liao, J. C. Estimation of nitric oxide production and reaction rates in tissue by use of a mathematical model. *Am J Physiol-Heart C* 43, H2163-H2176 (1998).
19. Jo, Y. S. et al. RAFT homo- and copolymerization of N-acryloyl-morpholine, piperidine, and azocane and their self-assembled structures. *Macromolecules* 41, 1140-1150 (2008).
20. Davies, K. M., Wink, D. A., Saavedra, J. E. & Keefer, L. K. Chemistry of the diazeniumdiolates. 2. Kinetics and mechanism of dissociation to nitric oxide in aqueous solution. *J. Am. Chem. Soc.* 123, 5473-5481 (2001).
21. Keefer, L. K. et al. Chemistry of the Diazeniumdiolates I. Structural and spectral characteristics of the [N(O)NO]⁻ functional group. *Nitric Oxide-Biol. Chem.* 5, 377-394 (2001).
22. Srinivasan, A. et al. Chemistry of the diazeniumdiolates. 3. Photoreactivity. *J. Am. Chem. Soc.* 123, 5465-5472 (2001).
23. Lee, V. M., Keefer, L. K. & Archer, M. C. An evaluation of the roles of metabolic denitrosation and α-hydroxylation in the hepatotoxicity of N-nitrosodimethylamine *Chem. Res. Toxicol.* 9, 1319-1324 (1996).
24. In a toxicological point of view, the main toxic effect of N-nitrosodimethylaamine comes from a subsequent reaction in a sequence of α-hydroxylation, formation of methyl diazonium ion, and DNA methylation. However, in piperazine-based system like pazh•NONOate, the cascades mentioned above cannot proceed due to the closed ring structure of homopiperazine.
25. Horstmann, A., Ph D Dissertation, Rheinischen Friedrich-Wilhelms-Universität, 2003.
26. Westedt, U. et al. Poly(vinyl alcohol)-graft-poly(lactide-co-glycolide) nanoparticles for local delivery of paclitaxel for restenosis treatment. *J. Control. Release* 119, 41-51 (2007).
27. Westedt, U. et al. Deposition of nanoparticles in the arterial vessel by porous balloon catheters: Localization by confocal laser scanning microscopy and transmission electron microscopy. *AAPS Pharmsci.* 4, 1-6 (2002).
28. Pulfer, S. K., Ott, D. & Smith, D. J. Incorporation of nitric oxide-releasing crosslinked polyethyleneimine microspheres into vascular grafts. *J. Biomed. Mater. Res.* 37, 182-189 (1997).
29. Masters, K. S. B. et al. Effects of nitric oxide releasing poly(vinyl alcohol) hydrogel dressings on dermal wound healing in diabetic mice. *Wound Repair Regen.* 10, 286-294 (2002).
30. Drago, R. S. & Karstetter, B. R. Reaction of nitrogen(ii) oxide with various primary and secondary amines. *J. Am. Chem. Soc.* 83, 1819-1822 (1961).
31. Duran, B. et al. Reduction of postoperative adhesions by N,O-carboxymethylchitosan and spermine NONOate in rats. *Exp. Anim.* 52, 267-272 (2003).
32. Zheng, H. et al. Design, synthesis, and evaluation of novel bifunctional iron-chelators as potential agents for neuroprotection in alzheimer's, parkinson's, and other neurodegenerative diseases. *Bioorg. Med. Chem.* 13, 773-783 (2005).
33. Jo, Y. S. et al. RAFT homo- and copolymerization of N-acryloyl-morpholine, piperidine, and azocane and their self-assembled structures. *Macromolecules* 41, 1140-1150 (2008).
34. Snyder, L. R. Classification of the solvent properties of common liquids. *J. Chromatogr., A* 92, 223-230 (1974).

It is claimed:

1. A vehicle for delivery of nitric oxide comprising:
a collection of micelles, each having an internal micelle core and a shell, the micelles comprising a polymer with N-diazeniumdiolate comprising NO complexed with secondary amines of the polymer, wherein the core comprises the polymer with the N-diazeniumdiolate, the shell comprises the polymer, and the polymer is water-soluble when free of complexed nitric oxide and is water-insoluble when complexed with the nitric oxide.

2. The vehicle of claim 1 wherein the polymer comprises piperazine moieties that contribute the secondary amines.

3. The vehicle of claim 2 wherein the piperazine moiety comprises

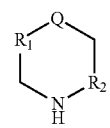

wherein Q comprises N in the piperazine ring and further is a linker to the polymer, and R1 or R2 are independently selected to be $CH_2$, $CH_2CH_2$, or $CH_3CH$.

4. The vehicle of claim 1 wherein the polymer is a block copolymer comprising a plurality of polymeric blocks, with a first block being a hydrophilic polymer that is free of secondary amines and a second block being a polymer that comprises the secondary amines.

5. The vehicle of claim 4 wherein the hydrophilic polymer comprises poly(N-acryloylmorpholine) or polyethylene glycol.

6. The vehicle of claim 4, wherein the second block is a copolymer.

7. The vehicle of claim 1 comprising a release rate half-life for the nitric oxide of between about 1 day to about 14 days.

8. The vehicle of claim 1 wherein the collection of micelles has a mean diameter in the range from about 10 nm to about 200 nm.

9. The vehicle of claim 1 wherein the collection of micelles is dried or frozen.

10. The vehicle of claim 1, with the vehicle being in a pharmaceutically acceptable composition and further comprising a pharmaceutically acceptable aqueous carrier that suspends the collection of micelles.

11. The vehicle of claim 4 wherein the shell comprises the hydrophilic polymer of the first block and the secondary amines are located on piperazines on the second block, with the core comprising said second block.

12. The vehicle of claim 1 wherein the micelle core comprises water and is internally depleted of water.

13. The vehicle of claim 1 wherein the micelle is internally free of water.

14. The vehicle of claim 1 wherein the NO release rate half life of the micelles is between about 14 days to about 30 days under physiological conditions.

15. A vehicle for delivery of nitric oxide comprising:
a collection of micelles having an internal micelle core and a shell, with the micelles each comprising a polymer with N-diazeniumdiolate comprising NO complexed with secondary amines of the polymer, wherein the core comprises the N-diazeniumdiolate and the shell comprises the polymer, and wherein the N-diazeniumdiolate comprises Poly[(N-acryloylmorpholine)-bl(sodium 1-[4-acryloyl-2,5-dimethylpipdiazen-1-yl]diazen-1-ium-1,2-diolate)].

16. A method of providing nitric oxide to a patient comprising introducing to the patient the vehicle of claim 1.

17. The method of claim 16 wherein introducing the micelles to the patient comprises delivering the micelles across a tissue surface of a patient under pressure.

18. The method of claim 17 wherein the pressure is applied through a catheter that delivers a fluid that comprises the micelles.

19. A method of making a nitric oxide vehicle comprising dissolving a polymer that comprises secondary amines in a solution and combining the polymer with nitric oxide in the solution to form a N-diazeniumdiolate comprising the nitric oxide complexed with the secondary amines, with the formation of the N-diazeniumdiolate causing the polymer to be at least partially insoluble in the solution and to form a collection of micelles that each has an internal core and a shell, with the core comprising the N-diazeniumdiolate, the shell comprising the polymer, and a NO release rate half life of the micelles being between about 1 day to about 30 days under physiological conditions.

20. The method of claim 19 wherein the polymer is a block copolymer of the polymer with secondary amines and a hydrophilic polymer.

21. The method of claim 20 further comprising removing the solution to make dry micelles.

\* \* \* \* \*